(12) United States Patent
Zhang et al.

(10) Patent No.: US 10,604,812 B2
(45) Date of Patent: Mar. 31, 2020

(54) MATERIALS AND METHODS FOR ASSESSING PROGRESSION OF PROSTATE CANCER

(71) Applicant: ABBOTT MOLECULAR INC., Des Plaines, IL (US)

(72) Inventors: Ying Zhang, Wilmette, IL (US); Ekaterina Pestova, Glenview, IL (US); Jing Du, Evanston, IL (US); Ping Liu, Wilmette, IL (US); Tracey Colpitts, Round Lake, IL (US)

(73) Assignee: Abbott Molecular Inc., Des Plaines, IL (US)

(*) Notice: Subject to any disclaimer, the term of this patent is extended or adjusted under 35 U.S.C. 154(b) by 0 days.

(21) Appl. No.: 16/005,228

(22) Filed: Jun. 11, 2018

(65) Prior Publication Data

US 2018/0291466 A1    Oct. 11, 2018

Related U.S. Application Data

(62) Division of application No. 14/788,195, filed on Jun. 30, 2015, now Pat. No. 9,994,912.

(60) Provisional application No. 62/020,990, filed on Jul. 3, 2014.

(51) Int. Cl.
*C12Q 1/6886*    (2018.01)

(52) U.S. Cl.
CPC ...... *C12Q 1/6886* (2013.01); *C12Q 2600/112* (2013.01); *C12Q 2600/118* (2013.01); *C12Q 2600/156* (2013.01)

(58) Field of Classification Search
CPC ............ C12Q 1/6886; C12Q 2600/156; C12Q 2600/118; C12Q 2600/112
See application file for complete search history.

(56) References Cited

U.S. PATENT DOCUMENTS

| | | | |
|---|---|---|---|
| 5,491,224 A | 2/1996 | Bittner et al. | |
| 5,658,730 A | 8/1997 | McGill et al. | |
| 5,756,696 A | 5/1998 | Gray et al. | |
| 6,613,510 B2 | 9/2003 | Jenkins et al. | |
| 7,037,667 B1 | 5/2006 | Afar et al. | |
| 7,425,414 B2 | 9/2008 | Coignet | |
| 7,452,727 B2 | 11/2008 | Henning et al. | |
| 7,718,369 B2 | 5/2010 | Tomlins et al. | |
| 8,211,645 B2 | 7/2012 | Tomlins et al. | |
| 8,257,924 B2 | 9/2012 | Hessels et al. | |
| 8,580,509 B2 | 11/2013 | Tomlins et al. | |
| 2003/0091994 A1* | 5/2003 | Jenkins ............... | C12Q 1/6886 435/6.11 |
| 2003/0165895 A1 | 9/2003 | Czerniak et al. | |
| 2003/0225528 A1 | 12/2003 | Baker et al. | |
| 2005/0252773 A1 | 11/2005 | McBride et al. | |
| 2006/0234259 A1 | 10/2006 | Rubin et al. | |
| 2007/0237770 A1 | 10/2007 | Lai et al. | |
| 2008/0131885 A1 | 6/2008 | Pratilas et al. | |
| 2009/0069194 A1 | 3/2009 | Ramakrishnan | |
| 2009/0208937 A1 | 8/2009 | Chinnaiyan et al. | |
| 2009/0239221 A1 | 9/2009 | Chinnaiyan et al. | |
| 2010/0215638 A1 | 8/2010 | Iljin et al. | |
| 2010/0233691 A1 | 9/2010 | Bankaitis-Davis et al. | |
| 2011/0028336 A1 | 2/2011 | Chinnaiyan et al. | |
| 2011/0097717 A1 | 4/2011 | Bankaitis-Davis | |
| 2011/0230361 A1 | 9/2011 | Moreno et al. | |
| 2011/0265197 A1 | 10/2011 | Depinho et al. | |
| 2011/0281263 A1 | 11/2011 | Matthiesen et al. | |
| 2011/0306514 A1 | 12/2011 | Hewitt et al. | |
| 2012/0009581 A1 | 1/2012 | Bankaitis-Davis et al. | |
| 2012/0015839 A1 | 1/2012 | Chinnaiyan | |
| 2012/0039889 A1 | 2/2012 | Rubin et al. | |
| 2012/0041274 A1 | 2/2012 | Stone et al. | |
| 2012/0065085 A1 | 3/2012 | Pestova et al. | |
| 2012/0214684 A1 | 8/2012 | Vieweg et al. | |
| 2012/0220672 A1 | 8/2012 | Pestano et al. | |
| 2012/0295809 A1 | 11/2012 | Tomlins et al. | |
| 2013/0005837 A1 | 1/2013 | Moreno et al. | |
| 2013/0029860 A1 | 1/2013 | Petrovics et al. | |
| 2013/0071843 A1* | 3/2013 | Squire ................. | C12Q 1/6841 435/6.11 |
| 2013/0171638 A1 | 7/2013 | Zhang et al. | |
| 2013/0196866 A1 | 8/2013 | Pestano et al. | |
| 2014/0037647 A1 | 2/2014 | Rubin et al. | |

(Continued)

FOREIGN PATENT DOCUMENTS

| | | |
|---|---|---|
| CA | 2375228 A1 | 12/2000 |
| CA | 2604844 A1 | 10/2006 |

(Continued)

OTHER PUBLICATIONS

Sun et al. The Prostate. 2007. 67:692-700. (Year: 2007).*
Attard G., et al., "Duplication of the Fusion of TMPRSS2 to ERG Sequences Identifies Fatal Human Prostate Cancer," Oncogene, 2008, vol. 27 (3), pp. 253-263.
Bova G.S., et al., "Homozygous Deletion and Frequent Allelic Loss of Chromosome 8p22 Loci in Human Prostate Cancer," Cancer Research, 1993, vol. 53 (17), 3869-3873.
Carter N.P., "Methods and Strategies for Analyzing Copy Number Variation Using DNA Microarrays," Nature Genetics, 2007, vol. 39 (Suppl. 7), pp. S16-S21.
Emmert-Buck M.R., et al., "Allelic Loss on Chromosome 8p12-21 in Microdissected Prostatic Intraepithelial Neoplasia," Cancer Research, 1995, vol. 55 (14), pp. 2959-2962.
Herrick J., et al., "Quantifying Single Gene Copy Number By Measuring Fluorescent Probe Lengths on Combed Genomic DNA,"Proceedings of the National Academy of Sciences, 2000, vol. 97 (1), pp. 222-227.

(Continued)

*Primary Examiner* — Joseph G. Dauner
(74) *Attorney, Agent, or Firm* — Casimir Jones, S.C.; Melissa E. Kolom

(57) ABSTRACT

Methods of distinguishing and identifying a patient with aggressive/indolent, prostatic adenocarcinoma comprising contacting a sample from the patient with a set of detectably labeled probes under hybridization conditions and determining the presence of chromosomal abnormalities in the sample; sets of probes for use in such methods; and kits comprising a set of probes and instructions for distinguishing or identifying a patient as having aggressive/indolent, prostatic adenocarcinoma.

6 Claims, 7 Drawing Sheets

(56) References Cited

U.S. PATENT DOCUMENTS

| | | | |
|---|---|---|---|
| 2014/0066325 A1 | 3/2014 | Liu et al. | |
| 2014/0109245 A1 | 4/2014 | Pestell | |

FOREIGN PATENT DOCUMENTS

| | | |
|---|---|---|
| CA | 2814598 A1 | 3/2007 |
| CA | 2719172 A1 | 10/2009 |
| EP | 1048740 A2 | 11/2000 |
| EP | 2083088 A2 | 7/2009 |
| EP | 2695950 A1 | 2/2014 |
| WO | WO-9318186 A1 | 9/1993 |
| WO | WO-9617958 A1 | 6/1996 |
| WO | WO-9620288 A1 | 7/1996 |
| WO | WO-9845479 A1 | 10/1998 |
| WO | WO-0077258 A1 | 12/2000 |
| WO | WO-2008023087 A2 | 2/2008 |
| WO | WO-2008121132 A2 | 10/2008 |
| WO | WO-2009140741 A1 | 11/2009 |
| WO | WO-2009144460 A1 | 12/2009 |
| WO | WO-2010056993 A2 | 5/2010 |
| WO | WO-2010099577 A1 | 9/2010 |
| WO | WO-2011037643 A2 | 3/2011 |
| WO | WO-2012013931 A1 | 2/2012 |
| WO | WO 2012145129 A2 | 3/2012 |
| WO | WO 2013101612 A1 | 7/2013 |
| WO | WO-2013173463 A1 | 11/2013 |
| WO | WO 2014028907 A1 | 2/2014 |

OTHER PUBLICATIONS

Irshad S., et al., "A Molecular Signature Predictive of Indolent Prostate Cancer," Science Translational Medicine, 2013, vol. 5 (202), pp. 202ra122 (14 pages).
Kagan J., et al., "Homozygous Deletions at 8p22 and 8p21 in Prostate Cancer Implicate These Regions as the Sites for Candidate Tumor Suppressor Genes," Oncogene, 1995, vol. 11 (10), pp. 2121-2126.
Kallioniemi A., et al., "Comparative Genomic Hybridization for Molecular Cytogenetic Analysis of Solid Tumors," Science, 1992, vol. 258 (5083), pp. 818-821.
Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.
Kumar J., et al., "Detection of Differential Gene Copy Number Using Denaturing High Performance Liquid Chromatography," Journal of Biochemical and Biophysical Methods, 2005, vol. 64 (3), pp. 226-234.
Morrison, L.E. et al., "Labeling Fluorescence in Situ Hybridization Probes for Genomic Targets," Methods in Molecular Biology, 2002, vol. 204, pp. 21-40.
Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.
Rigby P.W., et al., "Labeling Deoxyribonucleic Acid to High Specific Activity in Vitro by Nick Translation with DNA Polymerase I," Journal of Molecular Biology, 1997, vol. 113 (1), pp. 237-251.
Schouten J.P., et al., "Relative Quantification of 40 Nucleic Acid Sequences by Multiplex Ligation-dependent Probe Amplification," Nucleic Acids Research, 2002, vol. 30 (12), pp. e57.
Service R.F., "Gene Sequencing. The Race for the $1000 Genome," Science, 2006, vol. 311 (5767), pp. 1544-1546.
Shendure J., et al., "Advanced Sequencing Technologies: Methods and Goals," Nature Reviews. Genetics, 2004, vol. 5 (5), pp. 335-344.
Summersgill, et al., "Fluorescence and chromogenic in situ hybridization to detect genetic aberrations in formalin-fixed paraffin embedded material, including tissue microarrays." Nat Protoc. 2008;3(2):220-34.
Vogelstein B., et al., "Digital PCR," Proceedings of the National Academy of Sciences, 1999, vol. 96 (16), pp. 9236-9241.
Yoshimoto M., et al., "Fish Analysis of 107 Prostate Cancers Shows that PTEN Genomic Deletion is Associated with Poor Clinical Outcome," British Journal of Cancer, 2007, vol. 97 (5), pp. 678-685.
Choudhury A.D., et al., "The Role of Genetic Markers in the Management of Prostate Cancer," European Urology, 2012, vol. 62 (4), pp. 577-587.
Freier K., et al., "Recurrent FGFR1 Amplification and High FGFR1 Protein Expression in Oral Squamous Cell Carcinoma (OSCC)," Oral Oncology, 2007, vol. 43 (1), pp. 60-66.
International Search Report and Written Opinion for Application No. PCT/US2015/038761, dated Dec. 17, 2015, 6 pages/
Ishkanian A.S, et al., "Array CGH as a Potential Predictor of Radiocurability in Intermediate Risk Prostate Cancer," Acta Oncologica, 2010, vol. 49 (7), pp. 888-894.
Samaratunga H., et al., "What is the Molecular Pathology of Low-Risk Prostate Cancer?," World Journal of Urology, 2008, vol. 26 (5), pp. 431-436.
Yang F., et al., "FGFR1 is Essential for Prostate Cancer Progression and Metastasis.," Cancer Research, 2013, vol. 73 (12), pp. 3716-3724.
Zytovision Catalogue 2011, Feb. 1, 2011, XP055149936, p. 19.
Zafarana, et al., "Copy number alterations of c-Myc and PTEN are prognostic factors for relapse after prostate cancer radiotherapy." Cancer. Aug. 15, 2012;118(16):4053-62.
Perner, et al., "TMPRSS2:ERG fusion-associated deletions provide insight into the heterogeneity of prostate cancer." Cancer Res. Sep. 1, 2006;66(17):8337-41.
Otte, et al., "Abstract 3211: FGFR1 and FGFR2 gene copy number variations in prostate cancer." Cancer Research 2011, 71(8 Supplement): Abstract 3211.
Ahern, "Biochemical, reagent kits offer scientists good return on investment." The Scientist, 1995, 9(15):20.
Extended European Search Report dated Jul. 17, 2019, European Application No. 18248085.5, 8 pages.

* cited by examiner

MATERIALS AND METHODS FOR ASSESSING PROGRESSION OF PROSTATE CANCER

CROSS REFERENCE TO RELATED APPLICATIONS

This application is a divisional of U.S. patent application Ser. No. 14/788,195, filed Jun. 30, 2015, which claims priority to U.S. Provisional Application No. 62/020,990, filed Jul. 3, 2014, which are incorporated herein by reference in its entirety.

TECHNICAL FIELD

The present disclosure relates to methods for assessing progression of prostate cancer as well as sets of probes and kits useful in such methods.

BACKGROUND

Prostate cancer is the most common malignancy in men, and, after lung cancer, the second leading cause of death in men. There were an estimated 241,740 new cases in 2012 resulting in 28,170 deaths (www.cancer.gov). Most tumors are confined to the prostate, and most patients develop clinically insignificant prostate cancer, while other patients develop disseminated disease that is rapidly fatal.

Currently, about 30% of prostate cancer recurs after radical prostatectomy (RP). The identification of patients with a high recurrence risk is a challenge. The natural history of prostate carcinoma is extremely variable and rather unpredictable by existing methods (e.g., Gleason score). There is a need for effective predictors of tumor recurrence following surgery in order to determine whether a patient should be treated immediately with adjuvant therapy. Patients with tumors that are not biologically malignant would not benefit from such medical intervention. The foregoing, coupled with the significant morbidity associated with RP for apparently localized disease, and the high cost of RP, underscore the importance of discovering reliable molecular markers to predict the behavior of individual carcinomas.

Various markers and methods have been disclosed. For example, the measurement of the level of amplification of the HER-2/neu gene by fluorescent in situ hybridization (FISH) has been disclosed to be a method of determining the severity of prostate cancer (Int'l Pat. App. Pub. No. WO 1998/045479; "the '479 application"). In accordance with the method of the '479 application, a patient having five or more copies of Her-2/neu is treated aggressively. The determination of the presence of an amplified 8q24.1-24.2 chromosome band segment has been disclosed to be a method of diagnosing prostate cancer progression (U.S. Pat. No. 5,658,730). The determination of the loss of the 8p21-22 locus, a gain of chromosome 8, and an additional increase of the copy number of c-myc relative to the centromere copy number has been disclosed to be a method of prognosticating prostate cancer (U.S. Pat. No. 6,613,510). A gain of 8q24 (c-myc) and a loss of heterozygosity (LOH) of 8p21-22 (Bova et al., Cancer Res. 53: 3869-3873 (1993); and Kagan et al., Oncogene 11: 2121-2126 (1995); see, also, Emmert-Buck et al., Cancer Res. 55: 2959-2962 (1995), regarding allelic loss for 8p12-21) and 10q23 (PTEN) (Yoshimoto et al., Br. J. Cancer 97(5): 678-685 (Sep. 3, 2007); epub Aug. 14, 2007) also have been disclosed. Testing for the loss of heterozygosity at one or more loci on one or more of chromosomes 1-22 has been disclosed as a method of detecting a cell with a neoplastic or preneoplastic phenotype (U.S. Pat. App. Pub. No. 2003/0165895; "the '895 application"). The methods of the '895 application are disclosed as applicable to the detection of genetic changes relating to the progression of various cancers. Analysis of 20P1F12/TM-PRSS2, such as in a method of identifying evidence of a neoplasm, has been disclosed as useful for the assessment of prostate cancer (U.S. Pat. No. 7,037,667). Detecting a fusion between a 5' portion of TMPRSS2 and a 3' portion of ERG, ETV1, ETV4 or FLI1 and the presence of a PCA3 nucleic acid molecule has been disclosed as another method of identifying or characterizing prostate cancer (U.S. Pat. No. 8,580,509; see, also, U.S. Pat. Nos. 8,211,645 and 7,718,369 and U.S. Pat. App. Pub. Nos. 2012/0295809). A method of predicting recurrence, progression, and metastatic potential of prostate cancer comprising detecting three or more biomarkers selected from FOXO1A, SOX9, CLNS1A, PTGDS, XPO1, LETMD1, RAD23B, ABCC3, APC, CHES1, EDNRA, FRZB, HSPG2, and TMPRSS:ETV1 is disclosed in U.S. Pat. App. Pub. No. 2011/0230361 and Int'l Pat. App. Pub. No. WO 2010/056993. Screening prostate cancer patients with ERG-activation or ERG-translocation in order to evaluate responsiveness to anti-ERG therapy is disclosed in Int'l Pat. App. Pub. No. WO 2008/023087. The detection of TMPRSS2:ERG fusions, duplications thereof, and interstitial deletions 5' to ERG, along with Gleason score and PSA level, have been reported to enable stratification of patients with prostate cancer (Attard et al., Oncogene 27(3): 253-263 (January 2008); e-pub. Jul. 16, 2007). The detection of the overexpression of ERG, as well as the fusion of a 3' portion of ERG with a 5' portion of an androgen-regulated gene, such as TMPRSS2, NDRG1, SLC45A3 or PSA, has been disclosed for the early-stage diagnosis of prostate cancer (U.S. Pat. App. Pub. No. 2012/0220672; see, also, U.S. Pat. App. Pub. No. 2012/0039889 in re ERG:NDRG1 fusions). The use of HERPUD1:ERG and AX747630:ETV1 fusions in the identification of prostate cancer in a patient has been disclosed in U.S. Pat. App. Pub. No. 2012/0015839 (see, also, U.S. Pat. App. Pub. Nos. 2009/0239221 and 2009/0208937 for the use of other ERG and ETV1 gene fusions). The use of MIPOL1:ETV1 to detect prostate cancer is disclosed in U.S. Pat. App. Pub. No. 2011/0028336, whereas the use of ACSL3:ETS, such as ACSL3:ETV1, to diagnose a patient as having prostate cancer, as having aggressive prostate cancer, or as likely to develop prostate cancer and to assess whether a prostate tumor in a patient is suitable for anti-androgen therapy is disclosed in Int'l Pat. App. Pub. No. WO 2009/0144460 ("the '460 application"). Also disclosed in the '460 application is the use of an ETV1 fusion to assess Gleason score and/or clinical stage of prostate cancer and determine prognosis for prostate cancer. The detection of an ARG-ETS gene fusion, such as ARG:ERG and ARG:ETV1, has been disclosed as a method of screening for a prostate neoplasm (Canadian Pat. App. No. 2814598). U.S. Pat. App. Pub. No. 2012/0214684 discloses the use of a marker selected from OCT3/4, Nanong, Sox2, c-Myc, Klf4, Keratin 8, and uPAR in the detection of a neoplasia, such as prostate carcinoma, the characterization of the aggressiveness of prostate cancer, the monitoring of the effectiveness of therapy, and the selection of a treatment. Methods of assessing the progression of cancer and diagnosing carcinoma, melanoma, colon cancer, and prostate cancer by examining the level of an expression product of a gene selected from a group, which includes ETV1, among other methods, are disclosed in U.S. Pat. App. Pub. No. 2007/0237770. The measurement of at least two cell-cycle genes, such as AURKA, alone or in further combination with PTEN, has been disclosed in the classification of cancer, such as prostate cancer, in U.S. Pat. App. Pub. No. 2012/0041274. The use of MYC RNA, alone or in further combination with PTEN RNA, has been disclosed for the assessment of survivability in U.S. Pat. App. Pub. No. 2012/0009581. The determination of survival (e.g., diagnosis, prognosis, prediction of response, and/or relative survival rate) for a disease, such as cancer (e.g., prostate cancer), by quantification of at least two proteins, such as PTEN, is disclosed in U.S. Pat. App. Pub. No. 2011/0306514. The use of PCA3 and at least one other marker selected from a group, which includes TMPRSS2:ERG, to detect prostate cancer is disclosed in Int'l Pat. App. Pub. No. WO 2009/0140741. A method of diagnosing prostate cancer progression, or prostate cancer recurrence, comprising determining the presence of an amplified 8q24 chromosomal band segment is disclosed in Int'l Pat. App. Pub. No. 1996/020288. The use of a hybridization composition, which comprises a probe, a polar aprotic solvent other than DMSO, less than 10% formamide, and hybridization solution to detect a condition, such as cancer (e.g., prostate cancer), is disclosed in U.S. Pat. App. Pub. No. 2011/0281263. The probe in the hybridization composition can detect, for example, c-MYC, MYCN, PTEN, MDM2, FGFR1, AURKA, CEP8 or CEP10, among others. A method of characterizing prostate tissue by determining the levels of expression of a set of genes selected from ABP280 (FLNA), AMACR, AR, BM28, BUB3, CaMKK, CASPASE3, CDK7, DYNAMIN, E2F1, E-CADHERIN, EXPORTIN, EZH2, FAS, GAS7, GS28, ICBP90, ITGA5, JAGGED1, JAM1, KANADAPTIN, KLF6, KRIP1, LAP2, MCAM, MIB1 (MK167), MTA1, MUC1, MYSOIN-VI, P27, P63, PAXILLIN, PLCLN, PSA (KLK3), BAP27, RBBP, RIN1, SAPKα, TPD52, XIAP, and ZAG is disclosed in U.S. Pat. App. Pub. No. 2006/0234259; the method reportedly can involve prognosis, such as predicting prostate disease progression. Measurement of the level of two or more determinants selected from a list of 372 determinants in a method of assessing risk of recurrence of cancer or development of metastasis is disclosed in U.S. Pat. App. Pub. No. 2011/0265197; the method can reportedly involve measurement of a standard parameter, such as Gleason score for prostate cancer. The measurement of the expression level of ERG, alone or in further combination with the expression level of AMACR, in the diagnosis or prognosis of prostate cancer also has been disclosed in U.S. Pat. App. No. 2013/029860 (see, also, U.S. Pat. App. Pub. No. 2010/0215638 for the use of other ERG-associated genes in the screening of prostate cancer and the like). The detection of one or more biomarkers (e.g., RNA or protein) selected from a group consisting of CSPG2, WNT10B, E2F3, CDKN2A, TYMS, TGFB3, ALOX12, CD44, LAF4, CTNNA1, XPO1, PTGDAS, SOX9, RELA, EPB49, SIM2, EDNRA, RAD23B, FBP1, TNFRSF1A, CCNG2, LETMD1, NOTCH3, ETV1, BID, SIM2, ANXA1, BCL2, FOXO1A, CLNS1A, PTGDS, XPO1, LETMD1, RAD23B, ABCC3, APC, CHES1, EDNRA, FRZB, HSPG2, TMPRSS2:ETV1, CSPG2, CDKN2A, and others has been disclosed for the prediction of the recurrence, progression and metastatic potential of cancer (see U.S. Pat. App. Pub. No. 2013/0005837). The combination of FGFR1, PMP22, and CDKN1A has been reported to predict accurately the outcome of low Gleason-score tumors (Irshad et al., Sci. Transl. Med. 5(202): 202 (Sep. 11, 2013)). A method of diagnosing cancer, such as prostate cancer, comprising detecting differential expression of a gene selected from a group of 73 genes, which includes FGFR1, is disclosed in Canadian Pat. App. No. 2604844 (see, also, European Pat. App. No. 2083088). The use of PCA3 and a prostate-specific marker (e.g., NKX3.1), such as a ratio thereof, to prognose, assess tumor volume, monitor, determine risk of progression, and stage prostate cancer also has been disclosed (U.S. Pat. No. 8,257,924). The use of two or more genes selected from PSA/KLK3, PMEPA1, NKX3.1, ODC1, AMD1, and ERG to prognose prostate cancer, or evaluate androgen receptor signaling, such as by detection or measurement of expression, is disclosed in Canadian Pat. App. No. 2719172. The use of at least two molecular markers selected from her2/neu, p16, p53, Ki67, MN, mdm-2, bcl-2, and EGFR in an automatable method for identifying cancer cells and their precursor cells in a cell/tissue sample, such as a sample obtained from a prostate, is disclosed in U.S. Pat. No. 7,452,727. A method of prognosticating prostate cancer comprising determining a hybridization pattern of a set of chromosomal probes consisting of probes for 8p21-22, chromosome 8, and C-MYC is disclosed in U.S. Pat. No. 6,613,510. The use of antibodies to ERG, TFF3 and a high molecular weight cytokeratin to detect prostate cancer has been disclosed, including complete concordance between ERG expression by IHC and ERG gene status (i.e., rearrangement) by FISH, although no association between ERG/TFF3 expression and parameters, such as age, PSA, Gleason score, tumor stage, and biochemical recurrence, was observed (Int'l Pat. App. Pub. No. WO 2013/0173463). The use of expression levels of c-Myc, Ha-Ras, NeuT, and/or c-Src in the diagnosis of prostate cancer, the classification of a prostate cancer/tumor into a distinct prostate cancer subclass, and, in further combination with ErbB2, the stratification of a patient with a tumor, such as a prostate tumor, for clinical trial is disclosed in U.S. Pat. App. Pub. No. 2014/0109245. The use of two or more markers selected from TARDBP, TLN1, PARK7, ISPI1, CALD1, p73, PTEN, PXN, PEX10, KL3, DBN1, NFAT1, B-Tubulin, SOS1, HSF4, TOP1, HSPA1A, ACID2, STAT2, p53, CHD3 CASP8, STX6, AR, GAPDHS, cyclin D1, and CCNA2 to evaluate diagnostically a subject for prostate cancer is disclosed in U.S. Pat. App. Pub. No. 2014/0066325. A method of subtyping prostate cancer (e.g., risk of developing lethal neuroendocrine prostate cancer (NEPC)) involving the determination of the overexpression/amplification of AURKA and/or MYCN, alone or in further combination with ERG rearrangement, is disclosed in U.S. Pat. App. Pub. No. 2014/037647. The use of five or more markers selected from HOXA7, AURKA, NEK2, FOXM1B, CCNB1, CEP55, CENPA, DNMT3B, DNMT1, HELLS, MAPK8, BMI1, ITGB1, IVL, and CTNNB1 to diagnose, or monitor progression of, cancer, such as prostate cancer, is disclosed in Int'l Pat. App. Pub. No. 2012/013931. The detection of a break in the sequence of human chromosome 12q24 at the SMRT gene locus using FISH has been disclosed as a method of determining the likelihood of prostate cancer metastasis (U.S. Pat. No. 7,425,414). The determination of the level of a constituent, such as PTEN RNA, has been disclosed in the evaluation of prostate cancer, the assessment/monitoring of response to therapy in a patient with prostate cancer, and the monitoring of the progression of prostate cancer (Int'l Pat. App. Pub. No. WO 2008/121132). The detection of increased expression of ERG and decreased expression of PTEN, such as by detecting mRNA, protein, or alteration(s) in genomic sequence(s) (e.g., amplification, deletion, or fusion), to determine the aggressiveness of prostate cancer or that the prostate cancer has penetrated, or will likely penetrate, the prostatic capsule is disclosed in U.S. Pat. App. Pub. No. 2013/0196866 as is the detection of decreased expression of PTEN to determine recurrence of prostate cancer. The use of (i) MYC, PTEN, CEP8 and CEP7, (ii) MYC, LPL, PTEN, and CEP8, or (iii) MYC and CEP8 in the detection of prostate cancer is disclosed in U.S. Pat. App. Pub. No. 2013/0171638. The detection of the over-expression of PITX2 has been disclosed as a method for diagnosing the presence or risk of prostate cancer and, in combination with at least one other factor, such as PSA or Gleason grade, as a method for prognosticating prostate cancer (Int'l Pat. App. Pub. No. WO 2010/099577). The identification of an increased level of a nucleic acid or polypeptide selected from OCT3/4, Nanog, Sox2, c-myc, KIf4, keratin 8, and uPAR has been disclosed as a method of identifying a prostate carcinoma, a method of characterizing the aggressiveness of a prostate cancer, a method of identifying a propensity for developing metastatic prostate cancer, and other methods (Int'l Pat. App. Pub. No. 2011/037643). A method of predicting the likelihood of recurrence of cancer following treatment in a patient comprising determining the expression level of p27, or its expression product, is disclosed in U.S. Pat. App. Pub. No. 2003/0225528, whereas a method for determining the aggressiveness of prostate carcinoma comprising detecting p27 protein is disclosed in Int'l Pat. App. Pub. No. WO 2000/077258, which also discloses a method for determining the rate of proliferation of prostate cancer comprising detecting MDM2 expression (see, also, Canadian Pat. App. No. 2,375,228). A method of detecting a cell with a neoplastic or preneoplastic phenotype comprising testing a sample for loss of heterozygosity (LOH) at one or more loci on one or more chromosomes, such as those which are related to progression from preneoplasia to invasive carcinoma, is disclosed in U.S. Pat. App. Pub. No. 2003/0165895. A method of evaluating prostate cancer comprising quantitatively measuring at least one RNA (e.g., MYC) under repeatable conditions such that the measurement distinguishes prostate cancer from melanoma, lung cancer, and colon cancer with at least 75% accuracy is disclosed in U.S. Pat. App. Pub. No. 20111/097717 (see, also, U.S. Pat. App. Pub. No. 2010/0233691). A panel of isolated cancer biomarkers consisting of DUSP6, SPRY2 and one or more biomarkers selected from a group of approximately 33 genes, which includes ETV1, is disclosed in U.S. Pat. App. Pub. No. 2008/0131885.

In view of the foregoing, there remains a need for more reliable and informative prognostic methods in the management of prostate cancer. The present disclosure seeks to provide sets of markers, as well as methods of use and kits comprising the sets of markers, for the assessment of the progression of prostate cancer. This and other objects and advantages, as well as inventive features, will become apparent from the detailed description provided herein.

SUMMARY

A method of distinguishing between a patient with aggressive, prostatic adenocarcinoma and a patient with indolent, prostatic adenocarcinoma is provided. The method comprises:

(a) contacting a sample from the patient with:
(i) a set of detectably labeled probes consisting of a locus-specific probe for MYC and a locus-specific probe for FGFR1,
(ii) a set of detectably labeled probes comprising a locus-specific probe for MYC, a locus-specific probe for FGFR1, and a break-apart probe for ERG,
(iii) a set of detectably labeled probes comprising a locus-specific probe MYC, a locus-specific probe for FGFR1, a break-apart probe for ERG, and a locus-specific probe for PTEN,
(iv) a set of detectably labeled probes comprising a locus-specific probe for MYC, a locus-specific probe for FGFR1, a break-apart probe for ERG, and a locus-specific probe for MYCN, or
(v) a set of detectably labeled probes comprising a locus-specific probe for MYC, a locus-specific probe for FGFR1, a break-apart probe for ERG, and a locus-specific probe for MDM2,
(vi) a set of detectably labeled probes comprising a locus-specific probe for MYC, a locus-specific probe for FGFR1, a break-apart probe for ERG, and a locus-specific probe for NKX3.1,
(vii) a set of detectably labeled probes comprising a locus-specific probe for MYC, a break-apart probe for ETV1, a locus-specific probe for FGFR1, and a locus-specific probe for P27,
(viii) a set of detectably labeled probes comprising a locus-specific probe for MYC, a locus-specific probe for FGFR1, a locus-specific probe for PTEN, and a chromosome enumeration probe for chromosome 8 (CEP8),
(ix) a set of detectably labeled probes comprising a chromosome enumeration probe for chromosome 8, a locus-specific probe for MYC, a break-part probe for ERG, and a locus-specific probe for FGFR1,
(x) a set of detectably labeled probes comprising a chromosome enumeration probe for chromosome 8, a locus-specific probe for MYC, a break-apart probe for ERG, and a locus-specific probe for NKX3.1,
(xi) a set of detectably labeled probes comprising a chromosome enumeration probe for chromosome 8, a locus-specific probe for MYC, a break-apart probe for ERG, and a locus-specific probe for FGFR1,
(xii) a set of detectably labeled probes comprising a chromosome enumeration probe for chromosome 8, a locus-specific probe for MYC, a break-apart probe for ERG, and a locus-specific probe for MYCN,
(xiii) a set of detectably labeled probes comprising a chromosome enumeration probe for chromosome 8, a locus-specific probe for MYC, a break-apart probe for ERG, and a locus-specific probe for MDM2,
(xiv) a set of detectably labeled probes comprising a chromosome enumeration probe for chromosome 8, a locus-specific probe for MYC, a break-apart probe for ETV1, and a locus-specific probe for FGFR1,
(xv) a set of detectably labeled probes comprising a locus-specific probe for AURKA, a locus-specific probe for MYC, a break-apart probe for ERG, and a locus-specific probe for FGFR1,
(xvi) a set of detectably labeled probes comprising a chromosome enumeration probe for chromosome 8, a locus-specific probe for MYC, a break-apart probe for ERG, and a locus-specific probe for PTEN,
(xvii) a set of detectably labeled probes comprising a locus-specific probe for MYC, a break-apart probe for ERG, a locus-specific probe for FGFR1, and a locus-specific probe for P27, or
(xviii) a set of detectably labeled probes comprising a locus-specific probe for AURKA, a chromosome enumeration probe for chromosome 8, a locus-specific probe for MYC, and a break-apart probe for ERG, under hybridizing conditions, wherein the locus-specific probe for FGFR1 in the sets of (i)-(vi), (viii), (xi), (xiv), (xv), and (xvii) is used to determine % loss of FGFR1, wherein the locus-specific probe for FGFR1 in the sets of (vii), (ix), and, as an alternative to % loss of FGFR1, (xiv), is used to determine % gain of FGFR1, wherein CEP8 in the sets of (ix)-(xiv), (xvi), and (xviii) is used to determine % loss of CEP8, wherein the locus-specific probe for PTEN in sets (iii) and (viii) is used to determine % homozygous loss of PTEN, wherein the locus-specific probe for PTEN in set (xvi) is used to determine % loss of PTEN, and wherein the locus-specific probe for FGFR1 and CEP8 in the sets of (viii), and as an alternative to % gain of FGFR1, (ix), are used to determine % loss of FGFR1/CEP8 ratio, and (b) determining the presence of a chromosomal abnormality in the sample, wherein a MYC % gain (% gain is % of cells with MYC copy numbers >2) of greater than or equal to two to less than or equal to 30, wherein a FGFR1% loss (% loss is % of cells with FGFR copy numbers <2) of greater than or equal to 15 to less than or equal to 40, wherein a FGFR1% gain (% gain is % of cells with FGFR copy numbers >2) of greater than or equal to two to less than or equal to 46, wherein a CEP8% loss (% loss is % of cells with CEP8 copy numbers <2) of greater than or equal to 21 to less than or equal to 36, wherein a CEP8% gain (% gain is % of cells with CEP8 copy numbers >2) of greater than or equal to 15 to less than or equal to 40, wherein a FGFR1/CEP8% loss of greater than or equal to 13 to less than or equal to 72, wherein a PTEN % homozygous loss (% homozygous loss is % of cells with PTEN copy numbers of zero) of greater than or equal to two to less than or equal to 40, wherein a PTEN % loss (% loss is % of cells with PTEN copy number of less than two) of greater than or equal to 10 to less than or equal to 50, wherein a ERG 2+Edel of greater than or equal to one to less than or equal to 30, wherein a MYCN % gain (% gain is % of cells with MYCN copy numbers >2) of greater than or equal to two to less than or equal to 30, wherein a MDM2% gain (% gain is % of cells with MDM2 copy numbers >2) of greater than or equal to two to less than or equal to 20, wherein a NKX3.1% loss (% loss is % of cells with NKX3.1 copy numbers <2) of greater than or equal to 10 to less than or equal to 50, wherein an ETV1% translocation/deletion of greater than or equal to 1 to less than or equal to 20, wherein a P27% loss (% loss is % of cells with P27 copy numbers <2) of greater than or equal to 10 to less than or equal to 50, or wherein an AURKA % gain (% gain is % of cells with AURKA copy numbers >2) of greater than or equal to 1 to less than or equal to 20 indicates that the patient has a high risk of developing aggressive, prostatic adenocarcinoma, whereas none of the above indicates that the patient has indolent, prostatic adenocarcinoma. If a patient has had a prostatectomy, the determination of the presence of a chromosomal abnormality in the sample indicates that the patient has a high risk of recurrence or metastasis, in which case the method can further comprise recommending that the patient consult his physician for immediate treatment to inhibit or prevent recurrence or metastasis. If the patient has/is being initially diagnosed with prostate cancer and the patient has a high risk of developing aggressive, prostatic adenocarcinoma, the method can further comprise recommending that the patient consult his physician for immediate treatment. If the patient has/is being initially diagnosed with prostate cancer and the patient has indolent, prostatic adenocarcinoma, the method can further comprise recommending active surveillance or watchful waiting.

A method of identifying a patient with a high risk of developing aggressive, prostatic adenocarcinoma is provided. The method comprises:

(a) contacting a sample from the patient with:
(i) a set of detectably labeled probes consisting of a locus-specific probe for MYC and a locus-specific probe for FGFR1,
(ii) a set of detectably labeled probes comprising a locus-specific probe for MYC, a locus-specific probe for FGFR1, and a break-apart probe for ERG,
(iii) a set of detectably labeled probes comprising a locus-specific probe MYC, a locus-specific probe for FGFR1, a break-apart probe for ERG, and a locus-specific probe for PTEN,
(iv) a set of detectably labeled probes comprising a locus-specific probe for MYC, a locus-specific probe for FGFR1, a break-apart probe for ERG, and a locus-specific probe for MYCN, or
(v) a set of detectably labeled probes comprising a locus-specific probe for MYC, a locus-specific probe for FGFR1, a break-apart probe for ERG, and a locus-specific probe for MDM2, under hybridizing conditions, and (b) determining the presence of chromosomal abnormalities in the sample. For (i) a MYC % gain (% gain is % of cells with MYC copy numbers >2) of greater than or equal to 26 and/or a FGFR1% loss (% loss is % of cells with FGFR1 copy numbers <2) of greater than or equal to 26, whereas for (ii) a MYC % gain (% gain is % of cells with MYC copy numbers >2) of greater than or equal to 14, a FGFR1% loss (% loss is % of cells with FGFR1 copy numbers <2) of greater than or equal to 26, and/or an ERG % 2+Edel of greater than or equal to 10, for (iii) a MYC % gain (% gain is % of cells with MYC copy numbers >2) of greater than or equal to eight, a FGFR1% loss (% loss is % of cells with FGFR1 copy numbers <2) of greater than or equal to 26, an ERG % 2+Edel of greater than or equal to 10, and/or a PTEN % homozygous loss of greater than or equal to 20, for (iv) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MYCN % gain (% gain is % of cells with MYCN copy numbers >2) of greater than or equal to 20, or for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MDM2% gain (% gain is % of cells with MDM2 copy numbers >2) of greater than or equal to 10 indicates that the patient has a high risk of developing aggressive, prostate adenocarcinoma. The probe set of (i) can further consist of, or any of the probe sets of (ii)-(v) can further comprise, a chromosome enumeration probe for chromosome 8, a chromosome enumeration probe for chromosome 10, a locus-specific probe for AURKA, a locus-specific probe for NKX3.1, a locus-specific probe for P27, and/or a break-apart probe for ETV1. The method can further comprise obtaining a clinical parameter, such as a clinical parameter selected from the group consisting of a Gleason score, a tumor stage, a level of prostate-specific antigen (PSA), a nomogram, methylation status, mutation, and age of the patient, any of which can be combined with the determination of the presence of chromosomal abnormalities for prognosis. Thus, in an embodiment, the method comprises (a) contacting a sample from the patient with a set of detectably labeled probes comprising a locus-specific probe for MYC, a locus-specific probe for FGFR1, and a break-apart probe for ERG under hybridizing conditions, and (b) determining the presence of chromosomal abnormalities in the sample, wherein one or more of a MYC % gain (% gain is % of cells with MYC copy numbers >2) of greater than or equal to 14, an FGFR1% loss (% loss is % of cells with FGFR1 copy numbers <2) of greater than or equal to 26, and a ERG % 2+Edel of greater than or equal to 10 indicates that the patient has a high risk of developing aggressive, prostatic adenocarcinoma.

A method of identifying a patient with indolent, prostatic adenocarcinoma is also provided. The method comprises:
(a) contacting a sample from the patient with:
  (i) a set of detectably labeled probes consisting of a locus-specific probe for MYC and a locus-specific probe for FGFR1,
  (ii) a set of detectably labeled probes comprising a locus-specific probe for MYC, a locus-specific probe for FGFR1, and a break-apart probe for ERG,
  (iii) a set of detectably labeled probes comprising a locus-specific probe MYC, a locus-specific probe for FGFR1, a break-apart probe for ERG, and a locus-specific probe for PTEN,
  (iv) a set of detectably labeled probes comprising a locus-specific probe for MYC, a locus-specific probe for FGFR1, a break-apart probe for ERG, and a locus-specific probe for MYCN, or
  (v) a set of detectably labeled probes comprising a locus-specific probe for MYC, a locus-specific probe for FGFR1, a break-apart probe for ERG, and a locus-specific probe for MDM2, under hybridizing conditions, and
(b) determining the presence of chromosomal abnormalities in the sample. For (i) a MYC % gain (% gain is % of cells with MYC copy numbers >2) of greater than or equal to two and/or a FGFR1% loss (% loss is % of cells with FGFR1 copy numbers <2) of greater than or equal to 10, whereas for (ii) a MYC % gain (% gain is % of cells with MYC copy numbers >2) of greater than or equal to two, a FGFR1% loss (% loss is % of cells with FGFR1 copy numbers <2) of greater than or equal to 10, and/or an ERG % 2+Edel of greater than or equal to two, for (iii) a MYC % gain (% gain is % of cells with MYC copy numbers >2) of greater than or equal to two, a FGFR1% loss (% loss is % of cells with FGFR1 copy numbers <2) of greater than or equal to 10, an ERG % 2+Edel of greater than or equal to 10, and/or a PTEN % homozygous loss of greater than or equal to 20, for (iv) a MYC % gain (% gain is % of cells with MYC copy numbers >2) of greater than or equal to two, a FGFR1% loss (% loss is % of cells with FGFR1 copy numbers <2) of greater than or equal to 18, an ERG % 2+Edel of greater than or equal to two, and/or a MYCN % gain (% gain is % of cells with MYCN copy numbers >2) of greater than or equal to 20, or for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to two, and/or a MDM2% gain (% gain is % of cells with MDM2 copy numbers >2) of greater than or equal to three indicates that the patient has a high risk of developing aggressive, prostatic adenocarcinoma and none of the foregoing indicates that the patient has indolent, prostatic adenocarcinoma. The probe set of (i) can further consist of, or any of the probe sets of (ii)-(v) can further comprise, a chromosome enumeration probe for chromosome 8, a chromosome enumeration probe for chromosome 10, a locus-specific probe for AURKA, a locus-specific probe for NKX3.1, a locus-specific probe for P27, and/or a break-apart probe for ETV1. The method can further comprise obtaining a clinical parameter, such as a clinical parameter selected from the group consisting of a Gleason score, a tumor stage, a level of PSA, a nomogram, methylation status, mutation, and age of the patient, any of which can be combined with the determination of the presence of chromosomal abnormalities for prognosis. Thus, in an embodiment, the method comprises (a) contacting a sample from the patient with a set of detectably labeled probes comprising a locus-specific probe for MYC, a locus-specific probe for FGFR1, a locus-specific probe for PTEN, and a break-apart probe for ERG under hybridizing conditions, and (b) determining the presence of chromosomal abnormalities in the sample, wherein one or more of a MYC % gain (% gain is % of cells with MYC copy numbers >2) of greater than or equal to two, an FGFR1% loss (% loss is % of cells with FGFR1 copy numbers <2) of greater than or equal to 10, a PTEN % homozygous loss of greater than or equal to 20, and a ERG % 2+Edel of greater than or equal to 10 indicates that the patient has a high risk of developing aggressive, prostatic adenocarcinoma and none of the foregoing indicates that the patient has indolent, prostatic adenocarcinoma.

A set of probes is also provided. In one embodiment, the set of probes is:
(i) a set of detectably labeled probes consisting of a locus-specific probe for MYC and a locus-specific probe for FGFR1,
(ii) a set of detectably labeled probes comprising a locus-specific probe for MYC, a locus-specific probe for FGFR1, a break-apart probe for ERG, and a locus-specific probe for NKX3.1,
(iii) a set of detectably labeled probes comprising a locus-specific probe for MYC, a break-apart probe for ETV1, a locus-specific probe for FGFR1, and a locus-specific probe for P27,
(iv) a set of detectably labeled probes comprising a locus-specific probe for MYC, a locus-specific probe for FGFR1, a locus-specific probe for PTEN, and a chromosome enumeration probe for chromosome 8,
(v) a set of detectably labeled probes comprising a chromosome enumeration probe for chromosome 8, a locus-specific probe for MYC, a break-part probe for ERG, and a locus-specific probe for FGFR1,
(vi) a set of detectably labeled probes comprising a chromosome enumeration probe for chromosome 8, a locus-specific probe for MYC, a break-apart probe for ERG, and a locus-specific probe for NKX3.1,
(vii) a set of detectably labeled probes comprising a chromosome enumeration probe for chromosome 8, a locus-specific probe for MYC, a break-apart probe for ERG, and a locus-specific probe for FGFR1,
(viii) a set of detectably labeled probes comprising a chromosome enumeration probe for chromosome 8, a locus-specific probe for MYC, a break-apart probe for ERG, and a locus-specific probe for MYCN, (ix) a set of detectably labeled probes comprising a chromosome enumeration probe for chromosome 8, a locus-specific probe for MYC, a break-apart probe for ERG, and a locus-specific probe for MDM2, (x) a set of detectably labeled probes comprising a chromosome enumeration probe for chromosome 8, a locus-specific probe for MYC, a break-apart probe for ETV1, and a locus-specific probe for FGFR1, (xi) a set of detectably labeled probes comprising a locus-specific probe for AURKA, a locus-specific probe for MYC, a break-apart probe for ERG, and a locus-specific probe for FGFR1, (xii) a set of detectably labeled probes comprising a chromosome enumeration probe for chromosome 8, a locus-specific probe for MYC, a break-apart probe for ERG, and a locus-specific probe for PTEN, (xiii) a set of detectably labeled probes comprising a locus-specific probe for MYC, a break-apart probe for ERG, a locus-specific probe for FGFR1, and a locus-specific probe for P27, or (xiv) a set of detectably labeled probes comprising a locus-specific probe for AURKA, a chromosome enumeration probe for chromosome 8, a locus-specific probe for MYC, and a break-apart probe for ERG. The set of probes can further comprise a detectably labeled chromosome enumeration probe for chromosome 8, a detectably labeled chromosome enumeration probe for chromosome 10, a detectably labeled locus-specific probe for AURKA, a detectably labeled locus-specific probe for NKX3.1, a detectably labeled locus-specific probe for P27, and/or a detectably labeled break-apart probe for ETV1.

In another embodiment, the set of probes comprises a detectably labeled, locus-specific probe for MYC, a detectably labeled, locus-specific probe for FGFR1, and a detectably labeled, break-apart probe for ERG. The set of probes can further comprise a detectably labeled, locus-specific probe for PTEN, a detectably labeled, locus-specific probe for MYCN, a detectably labeled, locus-specific probe for MDM2, a detectably labeled chromosome enumeration probe for chromosome 8, a detectably labeled chromosome enumeration probe for chromosome 10, a detectably labeled locus-specific probe for AURKA, a detectably labeled locus-specific probe for NKX3.1, a detectably labeled locus-specific probe for P27, and/or a detectably labeled break-apart probe for ETV1.

A kit is also provided. The kit comprises a set of probes, such as a set of probes as described above, that enables distinguishing between a patient with aggressive, prostatic adenocarcinoma and a patient with indolent, prostatic adenocarcinoma and instructions for carrying out an above-described method. Alternatively, the kit comprises a set of probes, such as a set of probes as described above, that enables identification of a patient with a high risk of developing aggressive, prostatic adenocarcinoma or identification of a patient with indolent adenocarcinoma and instructions for carrying out an above-described method.

In one embodiment, the kit comprises (a) a set of probes that enables identification of a patient with a high risk of developing aggressive, prostatic adenocarcinoma, wherein the set of probes comprises a detectably labeled, locus-specific probe for MYC, a detectably labeled, locus-specific probe for FGFR1, and a detectably labeled, break-apart probe for ERG, and (b) instructions for identifying a patient with aggressive, prostatic adenocarcinoma, wherein the instructions comprise determining in a sample obtained from the patient the presence of chromosomal abnormalities. One or more of a MYC % gain (% gain is % of cells with MYC copy numbers >2) of greater than 14, an FGFR1% loss (% loss is % of cells with FGFR1 copy numbers <2) of greater than 26, and a ERG % 2+Edel of greater than 10 indicate that the patient has a high risk of developing aggressive, prostatic adenocarcinoma.

In another embodiment, the kit comprises (a) a set of probes that enables identification of a patient with indolent, prostatic adenocarcinoma, wherein the set of probes comprises a detectably labeled, locus-specific probe for MYC, a detectably labeled, locus-specific probe for FGFR1, a detectably labeled, break-apart probe for ERG, and a detectably labeled, locus-specific probe for PTEN, and (b) instructions for identifying a patient with indolent, prostatic adenocarcinoma, wherein the instructions comprise determining in a sample obtained from the patient the presence of chromosomal abnormalities. One or more of a MYC % gain (% gain is % of cells with MYC copy numbers >2) of greater than two, an FGFR1% loss (% loss is % of cells with FGFR1 copy numbers <2) of greater than 10, a PTEN % homozygous loss of greater than 20, and a ERG % 2+Edel of greater than 10 indicates that the patient has a high risk of developing aggressive, prostatic adenocarcinoma. None of the foregoing indicates that the patient has indolent, prostatic adenocarcinoma.

DETAILED DESCRIPTION

Figure 1:
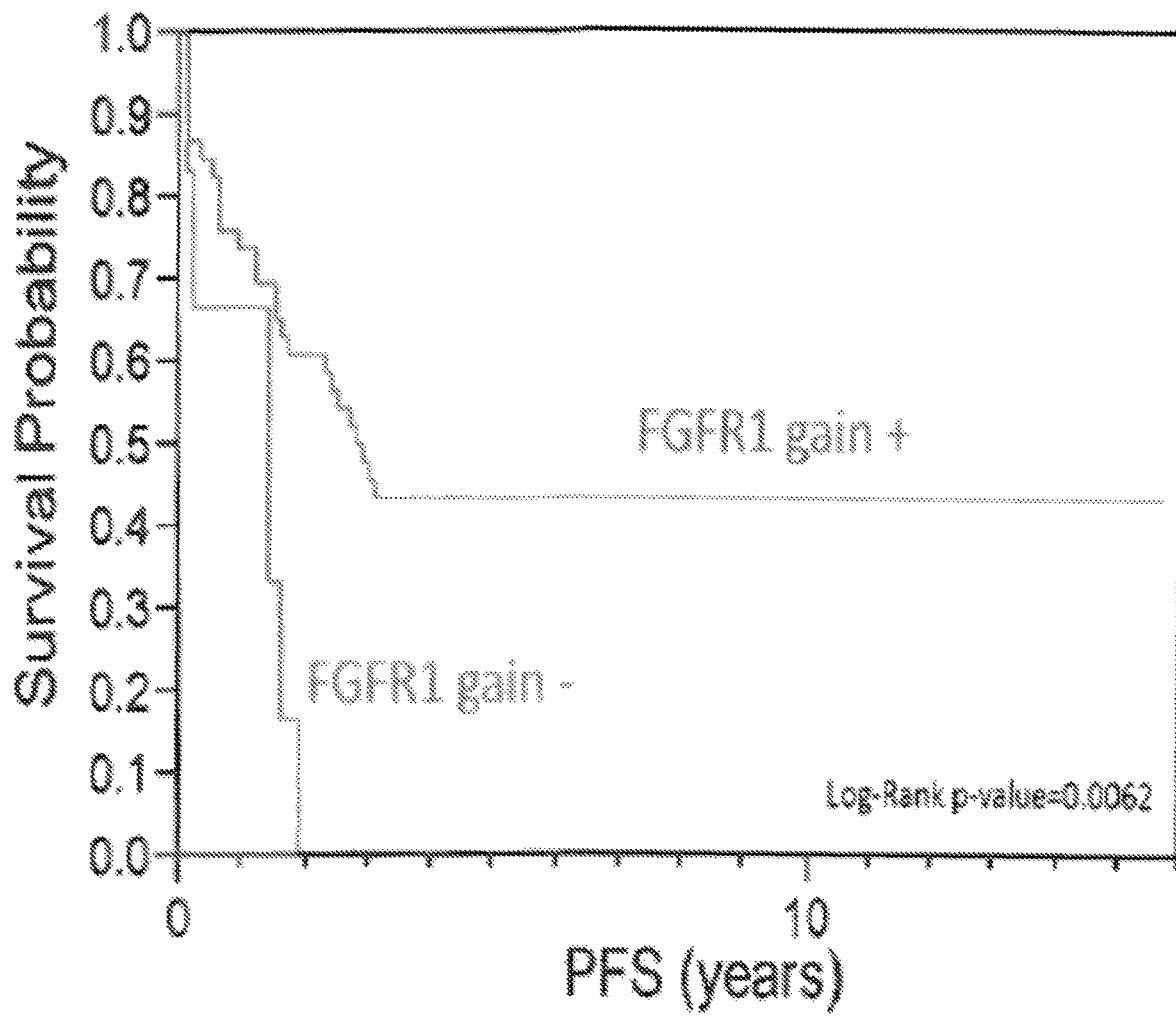
FIG. 1 is a KM curve (PFS (progression-free survival); years) vs. survival probability) of FGFR1 gain with a cutoff of six and a log-rank p-value of 0.0062.

The present disclosure provides sets of probes, kits comprising a set of probes and instructions for carrying out a method, a method of using a set of probes, or a kit comprising the set of probes, to distinguish or identify a patient with aggressive, prostatic adenocarcinoma or indolent, prostatic adenocarcinoma. The methods are useful in assessing risk of disease progression, including recurrence and death of disease (DOD), such as assessing risk of disease progression after treatment of prostatic adenocarcinoma (or prostate cancer), e.g., by radical prostatectomy. The methods also are useful in monitoring patients over time, such as patients, who have been identified as having indolent, prostatic adenocarcinoma, and patients, who have been identified as having aggressive, prostatic adenocarcinoma and are being, or will be, treated, such as with adjuvant therapy (e.g., androgen deprivation). The methods also can be used to confirm results of histological risk prediction and results of novel urine- or blood-based detection/screening methods. Thus, the methods can be used to identify patients for active surveillance or watchful waiting, potentially decrease the frequency of biopsies, and potentially reduce unnecessary radical prostatectomies, thereby improving quality of life for patients. The following terms are relevant to the present disclosure:

"2+Edel" may be used herein to refer to duplication of an ERG gene fusion, e.g., a TMPRSS2:ERG gene fusion, and interstitial deletion of sequences 5' to the ERG gene.

"About" refers to approximately a +/−10% variation from the stated value. It is to be understood that such a variation is always included in any given value provided herein, whether or not specific reference is made to it.

"Adenocarcinoma," "prostate adenocarcinoma," "carcinoma of the prostate," and "prostatic adenocarcinoma" may be used herein to refer to a malignant growth (i.e., cancer) in the prostate.

"AURKA" may be used herein to refer to the aurora kinase A gene. The Entrez Gene and HGNC cytogenetic bands are 20q13, whereas the Ensembl cytogenetic band is 20q13.2. Aliases for AURKA include ARK1, BTAK, STK15, STK6, AIK, PPP1R47, STK7, serine/threonine kinase 6, Aurora 2, Aurora-related kinase 1, Aurora/IPL1-related kinase 1, breast tumor-amplified kinase, serine/threonine-protein kinase 15, serine/threonine-protein kinase 6, serine/threonine-protein kinase aurora-A, ARK-1, AURA, hARK1, AURORA2, AurA, serine/threonine kinase 15, aurora/IPL1-like kinase, breast-tumor-amplified kinase, IPL1-related kinase, protein phosphatase 1 regulatory subunit 47, serine/threonine protein kinase 15, AIRK1, AYK1, EC2.7.11.1, and IAK1. "AURKA" is also used herein to refer to a probe or a set of probes used to determine a chromosomal abnormality involving AURKA, such as an increase in copy number. A probe for detecting a parameter involving AURKA, such as the copy number of AURKA, a copy number ratio involving AURKA, or the percentage gain of AURKA, by in situ hybridization, such as FISH, preferably hybridizes to the q13 region of chromosome 20 (20q13), which comprises the AURKA gene. DNA reference sequences include, but are not limited to, NC_000020.10 and NT_011362.10.

"Biomarker," as defined by the National Institutes of Health, is "a characteristic that is objectively measured and evaluated as an indicator of normal biologic processes, pathogenic processes, or pharmacologic responses to a therapeutic intervention."

"Break-apart probe" may be used herein to refer to a combination of two distinctly, detectably labeled probes, which enables the detection of a translocation. For example, one probe can hybridize at or near the 5' end of a given gene and fluoresce at one wavelength, whereas the other probe can hybridize at or near the 3' end of the given gene and fluoresce at a different wavelength. When the chromosome is in its native state, the colors combine as a single color, e.g., yellow. When the chromosome undergoes a translocation, the colors separate, e.g., red and green.

"Chromosome enumeration probe (CEP)" or "centromeric probe" may be used herein to refer to any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.). Specific examples of chromosome enumeration probes or centromeric probes include probes for chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, chromosome 20, chromosome 21, chromosome X, and chromosome Y. Specific examples of CEP® probes include CEP1, CEP2, CEP3, CEP4, CEP5, CEP6, CEP7, CEP8, CEP9, CEP10, CEP11, CEP12, CEP13, CEP14, CEP15, CEP16, CEP17, CEP18, CEP19, CEP20, CEP21, CEPX and CEPY.

"C-MYC" and "MYC" may be used interchangeably herein to refer to the c-myc oncogene. The Entrez Gene and Ensembl cytogenetic bands are 8q24.21, whereas the HGNC cytogenetic band is 8q24. Aliases include vHLHe39, c-Myc, v-myc avian myelocytomatosis viral oncogene homolog, Class E basic helix-loop-helix protein 39, proto-oncogene c-Myc, transcription factor p64, MRTL, avian myelocytomatosis viral oncogene homolog, myc proto-oncogene protein, myc-related translation/localization regulatory factor, and BHLHE39. MYC also may be used herein to refer to a probe or a set of probes that can be used to determine a chromosomal abnormality involving MYC, such as MYC copy number gain. A probe for detecting a parameter involving MYC, such as the copy number of MYC, a copy number ratio involving MYC, or the percentage gain of MYC, by in situ hybridization, such as FISH, preferably hybridizes to the q24 region of chromosome 8 (8q24), which comprises the MYC gene. DNA reference sequences include, but are not limited to, NC_000008.10 and NT_008046.16.

"Copy number" may be used herein to refer to a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"ERG" may be used herein to refer to the V-Ets avian erythroblastosis virus E26 oncogene homolog gene. The Entrez Gene and HGNC cytogenetic bands are 21q22.3, whereas the Ensembl genetic band is 21q22.2. Aliases include V-Ets avian erythroblastosis virus E26 oncogene related, transcriptional regulator ERG (transforming protein ERG), V-Ets erythroblastosis virus E26 oncogene like, TMPRSS2-ERG prostate cancer specific, erg-3, ets-related, p55, TMPRSS2/ERG fusion, transcriptional regulator ERG, V-Ets erythroblastosis virus E26 oncogene homolog, and transforming protein ERG. "ERG" also may be used herein to refer to a probe or a set of probes used to determine a chromosomal abnormality involving ERG. A probe for detecting a parameter involving ERG by in situ hybridization, such as FISH, preferably hybridizes to the q22 region of chromosome 21 (21q22), which comprises the ERG gene. Reference DNA sequences include NC_000021.8, NC_018932.2, and NT_011512.11.

"ETV1" may be used herein to refer to the Ets variant 1 gene. The Entrez Gene cytogenetic band is 7p21.3, whereas the Ensembl cytogenetic band is 7p21.2 and the HGNC cytogenetic band is 7p22. Aliases include Ets variant gene 1, Ets-related protein 81, ER81, and ETS translocation variant 1. "ETV1" also may be used herein to refer to a probe or a set of probes used to determine a chromosomal abnormality involving ETV1. A probe for detecting a parameter involving ETV1 by in situ hybridization, such as FISH, preferably hybridizes to the p21-22 region of chromosome 7 (7p21-22), which comprises the ETV1 gene. Reference DNA sequences include NC_000007.13, NT 007819.17, NC_018918.2, and NT_079592.2.

"FGFR1" may be used herein to refer to the fibroblast growth factor receptor 1 gene. The Entrez Gene and HGNC cytogenetic bands are 8p12, whereas the Ensembl cytogenetic band is 8p11.22. Aliases include FLT2, KAL2, Fms-related tyrosine kinase 2, basic fibroblast growth factor receptor 1, Fms-like tyrosine kinase 2, proto-oncogene C-Fgr, BFGFR, CEK, FGFBR, FGFR-1, FLG, FLT-2, HBGFR, bFGF-R-1, EC 2.7.10, EC 2.7.10.1, OGD, Pfeiffer syndrome, CD331, CD331 antigen, HH2, N-SAM, FGFR1/PLAG1 fusion, heparin-binding growth factor receptor, hydroxyaryl-protein kinase, N-SAM, N-sam, FGFR1/PLAG1 fusion, heparin-binding growth factor receptor, and hydroxyaryl-protein kinase. "FGFR1" also may be used herein to refer to a probe or a set of probes used to determine a chromosomal abnormality involving FGFR1. A probe for detecting a parameter involving FGFR1 by in situ hybridization, such as FISH, preferably hybridizes to the p11-12 regions of chromosome 8 (8p11-12), which comprises the FGFR1 gene. Reference DNA sequences include NC_000008.10, NT_167187.1, and NC_018919.2.

"Homozygous loss," "loss of heterozygosity," and "LOH" may be used interchangeably herein to refer to a loss or inactivation of both copies of an entire gene and surrounding chromosomal region.

"Labeled," "labeled with a detectable label," and "detectably labeled" may be used interchangeably herein to indicate that an entity (e.g., a probe) can be detected. "Label" and "detectable label" may be used herein to refer to a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" and "locus-specific identifier (LSI)" may be used interchangeably herein to refer to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"MDM2" may be used herein to refer to the MDM2 oncogene E3 ubiquitin protein ligase gene. The Entrez Gene cytogenetic band is 12q14.3-q15, whereas the Ensembl cytogenetic band is 12q15 and the HGNC cytogenetic band is 12q13-q14. Aliases include oncoprotein MDM2, MDM2 P53 binding protein homolog (mouse), MDM2 P53 E3 ubiquitin protein ligase homolog (mouse), MDM2 transformed 3T3 cell double minute 2 p53 binding protein (mouse), human homolog of mouse double minute 2 P53-binding protein, ACTFS, HDMX, human homolog of double minute 2 P53-binding protein, E3 ubiquitin-protein ligase MDM2, hdm2, MDM2 P53 E3 ubiquitin protein ligase homolog, MDM2 transformed 3T3 cell double minus 2 p53 binding protein, EC 6.3.2, Hdm2, double minute 2 protein, and P53 binding protein MDM2. "MDM2" also may be used herein to refer to a probe or a set of probes used to determine a chromosomal abnormality involving MDM2. A probe for detecting a parameter involving MDM2 by in situ hybridization, such as FISH, preferably hybridizes to the q13-15 regions of chromosome 12 (12q13-15), which comprises the FGFR1 gene. Reference DNA sequences include NC_000012.11, NT_029419.12, and NC_018923.2.

"MYCN" may be used herein to refer to the V-Myc avian myelocytomatosis viral oncogene neuroblastoma derived homolog gene. The Entrez Gene, Ensembl, and HGNC cytogenetic bands are 2p24.3. Aliases include NMYC, class E basic helix-loop-helix protein 37, bHLHe37, MODED, ODED, MYCNOT, N-myc, N-Myc proto-oncogene protein, neuroblastoma MYC oncogene, neuroblastoma-derived V-Myc avian myelocytomatosis viral related oncogene, oncogene NMYC, pp65/67, V-Myc avian myelocytomatosis viral related oncogene neuroblastoma derived, V-Myc myelocytomatosis viral related oncogene neuroblastoma derived, and BHLHE37. "MYCN" also may be used herein to refer to a probe or a set of probes used to determine a chromosomal abnormality involving MDM2. A probe for detecting a parameter involving MDM2 by in situ hybridization, such as FISH, preferably hybridizes to the p24 region of chromosome 2 (2p24), which comprises the MYCN gene. Reference DNA sequences include NC_000002.11, NC_018913.2, and NT_005334.16.

"NKX3.1" may be used herein to refer to the NK3 homeobox 1 gene. The Entrez Gene, Ensembl, and HGNC cytogenetic bands are 8p21.2. Aliases include NKX3-1, NKX3A, homeobox protein NK-3 homolog A, BAPX2, NK homeobox (Drosophila) family 3 A, NK3 transcription factor related locus 1 (Drosophila), NKX3, homeobox protein Nkx-3.1, NK homeobox family 3 A, NK3 transcription factor homolog A, and NK3 transcription factor related locus 1. "NKX3.1" also may be used herein to refer to a probe or a set of probes used to determine a chromosomal abnormality involving NKX3.1. A probe for detecting a parameter involving MDM2 by in situ hybridization, such as FISH, preferably hybridizes to the p21 region of chromosome 8 (8p21), which comprises the NKX3.1 gene. Reference DNA sequences include NC_000008.10, NC_018919.2, and NT_167187.1.

"Nucleic acid sample" may be used herein to refer to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"P27" may be used herein to refer to the cyclin-dependent kinase inhibitor 1B gene. The Entrez Gene and HGNC cytogenetic bands are 12p13.1-p12, whereas the Ensembl cytogenetic band is 12p13.1. Aliases include Kip1, KIP1, CDKN4, MEN4, MEN1B, P27KIP1, cyclin-dependent kinase inhibitor, and p27Kip1. "P27" also may be used herein to refer to a probe or a set of probes used to determine a chromosomal abnormality involving P27. A probe for detecting a parameter involving P27 by in situ hybridization, such as FISH, preferably hybridizes to the p13-12 region of chromosome 12 (12p13-12), which comprises the P27 gene. Reference DNA sequences include NC_000012.11, NC_018923.2, and NT_009714.17.

"Predetermined cutoff" and "predetermined level" may be used herein to refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/non-progression/improvement, etc.).

"Probe" may be used herein to refer to an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications, whereas a length of about $50-1\times10^5$ nucleotides can be preferred for chromosomal probes and a length of about 25,000 to about 800,000 nucleotides can be preferred for locus-specific probes. Generally speaking, a probe is detectably labeled, such as in accordance with methods described herein and known in the art.

"Prognosis" may be used herein to refer to a prediction of the probable course and/or outcome of a disease, such as the likelihood of recovery. Thus, prognosis encompasses an improvement in disease status, a worsening in disease status, and no change in disease status.

"Progression" may be used herein to refer to recurrence and/or death of disease (DOD).

"Prostate cancer" may be used herein to refer to all types of prostate cancer, such as adenocarcinoma, small cell carcinoma, squamous cell carcinoma, sarcoma, and transitional cell carcinoma. The majority of prostate cancer (around 95%) is adenocarcinoma. Prostate cancer is distinguished from prostatic intra-epithelial neoplasia (PIN, which is further distinguished as low-grade or high-grade), which is a precursor to prostate cancer. Small cell carcinoma and squamous cell carcinoma tend to be very aggressive in nature and do not lead to an increase in prostate-specific antigen (PSA). Transitional cell carcinoma rarely develops in the prostate but derives from primary tumors in the bladder and/or urethra.

"Prostatectomy" may be used herein to refer to removal of part or all of a prostate, alone or in further combination with other structures. A "simple" or "open" prostatectomy can consist of enucleation of a hyperplastic, prostatic adenoma. A "radical" prostatectomy can refer to removal en bloc of the entire prostate, the seminal vesicles, and the vas deferens. Such terms may be used interchangeable herein, and the use of one is not intended to exclude the other.

"PTEN" may be used herein to refer to the phosphatase and tensin homolog gene. The Entrez Gene cytogenetic band is 10q23.3, whereas the Ensembl cytogenetic band is 10q23.31, and the HGNC cytogenetic band is 10q23. Aliases include phosphatase and tensin-like protein, phosphatidylinositol 3,4,5-trisphosphate 3-phosphatase and dual-specificity protein phosphatase, PTEN1, mutated in multiple advanced cancers 1, MMAC1, MMAC1 phosphatase and tensin homolog deleted on chromosome 10, BZS, MHAM, TEP1, GLM2, 10q23del, CWS1, DEC, EC 3.1.3.16, EC 3.1.3.48, and EC 3.1.3.67. "PTEN" also may be used herein to refer to a probe or a set of probes used to determine a chromosomal abnormality involving PTEN. A probe for detecting a parameter involving PTEN by in situ hybridization, such as FISH, preferably hybridizes to the q23 region of chromosome 10 (10q23), which comprises the PTEN gene. Reference DNA sequences include NC_000010.10, NC_018921.2, and NT_030059.13.

"Risk of progression" may be used herein to refer to the risk of a worsening in disease status, recurrence, such as after remission, and death of disease (DOD).

"Section" of a tissue sample is a single part or piece of a tissue sample, e.g., a thin slice of tissue or cells cut from a tissue sample. Two or more sections of tissue samples may be taken and analyzed. If desired, a single section can be analyzed at various levels, e.g., morphological and molecular (e.g., nucleic acid and protein).

"Selectively hybridize to" (as well as "selective hybridization," "specifically hybridize to," and "specific hybridization") may be used herein to refer to the binding, duplexing, or hybridizing of a nucleic acid molecule preferentially to a particular nucleotide sequence under stringent conditions. The term "stringent conditions" may be used herein to refer to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, N.Y. (1993) ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual,* 3rd ed., Vol. 1-3, Cold Spring Harbor Laboratory, Cold Spring Harbor Press, N.Y. (2001)).

"Target sequence," "target region," and "nucleic acid target" may be used herein to refer to a nucleotide sequence that resides at a specific chromosomal location whose loss and/or gain, for example, is being determined.

The terminology used herein is for the purpose of describing particular embodiments only and is not otherwise intended to be limiting.

Methods of Distinguishing Patients with Aggressive Vs. Indolent Prostatic Adenocarcinoma, Identifying a Patient with Aggressive Prostatic Adenocarcinoma, and Identifying a Patient with Indolent Prostatic Adenocarcinoma A method of distinguishing between a patient with aggressive, prostatic adenocarcinoma and a patient with indolent, prostatic adenocarcinoma is provided. The method comprises:

(a) contacting a sample from the patient with:
(i) a set of detectably labeled probes consisting of a locus-specific probe for MYC and a locus-specific probe for FGFR1,
(ii) a set of detectably labeled probes comprising a locus-specific probe for MYC, a locus-specific probe for FGFR1, and a break-apart probe for ERG,
(iii) a set of detectably labeled probes comprising a locus-specific probe MYC, a locus-specific probe for FGFR1, a break-apart probe for ERG, and a locus-specific probe for PTEN,
(iv) a set of detectably labeled probes comprising a locus-specific probe for MYC, a locus-specific probe for FGFR1, a break-apart probe for ERG, and a locus-specific probe for MYCN, or
(v) a set of detectably labeled probes comprising a locus-specific probe for MYC, a locus-specific probe for FGFR1, a break-apart probe for ERG, and a locus-specific probe for MDM2,
(vi) a set of detectably labeled probes comprising a locus-specific probe for MYC, a locus-specific probe for FGFR1, a break-apart probe for ERG, and a locus-specific probe for NKX3.1,
(vii) a set of detectably labeled probes comprising a locus-specific probe for MYC, a break-apart probe for ETV1, a locus-specific probe for FGFR1, and a locus-specific probe for P27,
(viii) a set of detectably labeled probes comprising a locus-specific probe for MYC, a locus-specific probe for FGFR1, a locus-specific probe for PTEN, and a chromosome enumeration probe for chromosome 8 (CEP8),
(ix) a set of detectably labeled probes comprising a chromosome enumeration probe for chromosome 8, a locus-specific probe for MYC, a break-part probe for ERG, and a locus-specific probe for FGFR1,
(x) a set of detectably labeled probes comprising a chromosome enumeration probe for chromosome 8, a locus-specific probe for MYC, a break-apart probe for ERG, and a locus-specific probe for NKX3.1,
(xi) a set of detectably labeled probes comprising a chromosome enumeration probe for chromosome 8, a locus-specific probe for MYC, a break-apart probe for ERG, and a locus-specific probe for FGFR1,
(xii) a set of detectably labeled probes comprising a chromosome enumeration probe for chromosome 8, a locus-specific probe for MYC, a break-apart probe for ERG, and a locus-specific probe for MYCN,
(xiii) a set of detectably labeled probes comprising a chromosome enumeration probe for chromosome 8, a locus-specific probe for MYC, a break-apart probe for ERG, and a locus-specific probe for MDM2,
(xiv) a set of detectably labeled probes comprising a chromosome enumeration probe for chromosome 8, a locus-specific probe for MYC, a break-apart probe for ETV1, and a locus-specific probe for FGFR1,
(xv) a set of detectably labeled probes comprising a locus-specific probe for AURKA, a locus-specific probe for MYC, a break-apart probe for ERG, and a locus-specific probe for FGFR1,
(xvi) a set of detectably labeled probes comprising a chromosome enumeration probe for chromosome 8, a locus-specific probe for MYC, a break-apart probe for ERG, and a locus-specific probe for PTEN,
(xvii) a set of detectably labeled probes comprising a locus-specific probe for MYC, a break-apart probe for ERG, a locus-specific probe for FGFR1, and a locus-specific probe for P27, or
(xviii) a set of detectably labeled probes comprising a locus-specific probe for AURKA, a chromosome enumeration probe for chromosome 8, a locus-specific probe for MYC, and a break-apart probe for ERG, under hybridizing conditions, wherein the locus-specific probe for FGFR1 in the sets of (i)-(vi), (viii), (xi), (xiv), (xv), and (xvii) is used to determine % loss of FGFR1, wherein the locus-specific probe for FGFR1 in the sets of (vii), (ix), and, as an alternative to % loss of FGFR1, (xiv), is used to determine % gain of FGFR1, wherein CEP8 in the sets of (ix)-(xiv), (xvi), and (xviii) is used to determine % loss of CEP8, wherein the locus-specific probe for PTEN in sets (iii) and (viii) is used to determine % homozygous loss of PTEN, wherein the locus-specific probe for PTEN in set (xvi) is used to determine % loss of PTEN, and wherein the locus-specific probe for FGFR1 and CEP8 in the sets of (viii), and as an alternative to % gain of FGFR1, (ix), are used to determine % loss of FGFR1/CEP8 ratio, and (b) determining the presence of a chromosomal abnormality in the sample, wherein a MYC % gain (% gain is % of cells with MYC copy numbers >2) of greater than or equal to two to less than or equal to 30, wherein a FGFR1% loss (% loss is % of cells with FGFR copy numbers <2) of greater than or equal to 15 to less than or equal to 40, wherein a FGFR1% gain (% gain is % of cells with FGFR copy numbers >2) of greater than or equal to two to less than or equal to 46, wherein a CEP8% loss (% loss is % of cells with CEP8 copy numbers <2) of greater than or equal to 21 to less than or equal to 36, wherein a CEP8% gain (% gain is % of cells with CEP8 copy numbers >2) of greater than or equal to 15 to less than or equal to 40, wherein a FGFR1/CEP8% loss of greater than or equal to 13 to less than or equal to 72, wherein a PTEN % homozygous loss (% homozygous loss is % of cells with PTEN copy numbers of zero) of greater than or equal to two to less than or equal to 40, wherein a PTEN % loss (% loss is % of cells with PTEN copy number of less than two) of greater than or equal to 10 to less than or equal to 50, wherein a ERG 2+Edel of greater than or equal to one to less than or equal to 30, wherein a MYCN % gain (% gain is % of cells with MYCN copy numbers >2) of greater than or equal to two to less than or equal to 30, wherein a MDM2% gain (% gain is % of cells with MDM2 copy numbers >2) of greater than or equal to two to less than or equal to 20, wherein a NKX3.1% loss (% loss is % of cells with NKX3.1 copy numbers <2) of greater than or equal to 10 to less than or equal to 50, wherein ETV1% translocation/deletion of greater than or equal to 1 to less than or equal to 20, wherein a P27% loss (% loss is % of cells with P27 copy numbers <2) of greater than or equal to 10 to less than or equal to 50, or wherein an AURKA % gain (% gain is % of cells with AURKA copy numbers >2) of greater than or equal to 1 to less than or equal to 20 indicates that the patient has a high risk of developing aggressive, prostatic adenocarcinoma, whereas none of the above indicates that the patient has indolent, prostatic adenocarcinoma.

Another method of distinguishing aggressive, prostatic adenocarcinoma from indolent, prostatic carcinoma in a patient or patient population is provided. The patient can be an individual patient or a member of a patient population, such as a patient population that is being divided into groups, such as a group comprising patients having a high risk for developing aggressive, prostatic adenocarcinoma and a group comprising patients with indolent, prostatic adenocarcinoma. The method comprises (or consists of) (a) contacting a sample from a patient with a set of detectably labeled probes and (b) determining the presence of chromosomal abnormalities in the sample. The set of detectably labeled probes can comprise two, three, four, five, six, seven, eight, nine or ten probes selected from the group consisting of a locus-specific probe for MYC, a locus-specific probe for FGFR1, a chromosome enumeration probe for chromosome 8, a chromosome enumeration probe for chromosome 10, a locus-specific probe for PTEN, a break-apart probe (or telomeric (ERG Tel) and centromeric (ERG Cen) probes) for ERG, a locus-specific probe for NKX3.1, a locus-specific probe for MYCN, a locus-specific probe for MDM2, a locus-specific probe for P27, a break-apart probe for ETV1, a locus-specific probe for AURKA, and one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired.

The MYC probe can be used to determine MYC % gain (% gain is % of cells with MYC copy numbers >2), such as a MYC % gain of greater than or equal to two to less than or equal to 30. The FGFR1 probe can be used to determine FGFR1% loss (% loss is % of cells with FGFR1 copy numbers <2), such as FGFR1% loss of greater than or equal to 15 to less than or equal to 40. Additionally or alternatively, the FGFR1 probe can be used to determine FGFR1% gain (% gain is % of cells with FGFR1 copy numbers >2), such as FGFR1% gain of greater than or equal to two to less than or equal to 46. The CEP8 probe can be used to determine CEP8% loss (% loss is % of cells with CEP8 copy numbers <2), such as a CEP8% loss of greater than or equal to 21 to less than or equal to 36. Additionally or alternatively, the CEP8 probe can be used to determine CEP8% gain (% gain is % of cells with CEP8 copy numbers >2), such as a CEP8% gain of greater than or equal to 15 to less than or equal to 40. In this regard, the FGFR1 probe and the CEP8 probe can be used in combination to determine, for example, FGFR1/CEP8, such as a FGFR1/CEP8% loss of greater than or equal to 13 to less than or equal to 72. The PTEN probe can be used to determine PTEN % homozygous loss (% homozygous loss is % of cells with PTEN copy numbers of zero), such as a PTEN % homozygous loss of greater than or equal to two to less than or equal to 40; alternatively, the PTEN probe can be used to determine PTEN % loss (% loss is % of cells with PTEN copy number of less than two), such as PTEN % loss of greater than or equal to 10 to less than or equal to 50. The CEP10 probe can be used to determine CEP10% loss (% loss is % of cells with CEP10 copy numbers <2), such as a CEP10% loss of greater than or equal to 10 to less than or equal to 50. Additionally, or alternatively, the CEP10 probe can be used to determine CEP10% gain (% gain is % of cells with CEP10 copy numbers >2), such as a CEP10% gain of greater than or equal to 15 to less than or equal to 40. In this regard, the PTEN probe and the CEP10 probe can be used in combination to determine, for example PTEN/CEP10, such as a PTEN/CEP10% loss of greater than or equal to 10 to less than or equal to 50. The ERG probes can be used to determine % 2E+del of greater than greater than or equal to 1 to less than or equal to 30. The MYCN probe can be used to determine MYCN % gain (% gain is % of cells with MYCN copy numbers >2), such as a MYCN % gain of greater than or equal to two and less than or equal to 30. The MDM2 probe can be used to determine MDM2% gain (% gain is % of cells with MDM2 copy numbers >2), such as MDM2% gain of greater than or equal to two and less than or equal to 20. The NKX3.1 probe can be used to determine NKX3.1% loss (% loss is % of cells with NKX3.1 copy numbers <2), such as NKX3.1% loss of greater than or equal to 10 to less than or equal to 50. The ETV1 break-apart probe can be used to determine ETV1% single red (% single red is % of cells with ETV1 translocation or deletion), such as ETV1% single red of greater than or equal to one to less than or equal to 20. The P27 probe can be used to determine P27% loss (% loss is % of cells with P27 copy numbers <2), such as P27% loss of greater than or equal to 10 to less than or equal to 50. The AURKA probe can be used to determine AURKA % gain (% gain is % of cells with AURKA copy numbers >2), such as AURKA % gain of greater than or equal to 1 to less than or equal to 20.

If a patient has had a prostatectomy, the determination of the presence of a chromosomal abnormality in the sample indicates that the patient has a high risk of recurrence or metastasis, in which case the above methods can further comprise recommending that the patient consult his physician for immediate treatment to inhibit or prevent recurrence or metastasis. If a patient has/is being initially diagnosed with prostate cancer and the patient has a high risk of developing aggressive, prostatic adenocarcinoma, the above methods can further comprise recommending that the patient consult his physician for immediate treatment. If a patient has/is being initially diagnosed with prostate cancer and the patient has indolent, prostatic adenocarcinoma, the above methods can further comprise recommending active surveillance (e.g., a biopsy about every six months to a year) or watchful waiting (i.e., no active intervention).

The methods can further comprise obtaining a clinical parameter, such as a clinical parameter selected from the group consisting of a Gleason score, a tumor stage, a level of prostate-specific antigen (PSA), a nomogram, methylation status, mutation, and age of the patient, any of which can be combined with the determination of the presence of chromosomal abnormalities for prognosis. The above methods can further comprise monitoring a patient identified as having aggressive, prostatic adenocarcinoma during treatment by repeating (a) and (b) over a course of treatment. If the patient has already undergone a radical prostatectomy, the treatment can be an adjuvant treatment. Alternatively, the above methods can further comprise surveilling a patient identified as having indolent, prostatic adenocarcinoma by repeating (a) and (b) periodically. With regard to the above methods, the patient may have already been identified as having aggressive or indolent, prostatic adenocarcinoma by another method, such as a method selected from the group consisting of a histological examination of a sample of prostate cells, a method of detecting/screening a sample of urine for a marker of aggressive or indolent, prostatic adenocarcinoma, and a method of detecting/screening a sample of blood for a marker of aggressive or indolent, prostatic adenocarcinoma.

In view of the above, a method of identifying a patient with a high risk of developing aggressive, prostatic adenocarcinoma is also provided. The method comprises (or consists of) (a) contacting a sample from the patient with a set of detectably labeled probes comprising two, three, four, five or six probes selected from the group consisting of MYC, FGFR1, ERG, PTEN, MYCN, and MDM2 under hybridizing conditions and (b) determining the presence of chromosomal abnormalities in the sample. Examples of combinations of probes include, but are not limited to, (i) MYC and FGFR1, (ii) MYC, FGFR1, and ERG, (iii) MYC, FGFR1, ERG, and PTEN, (iv) MYC, FGFR1, ERG, and MYCN, and (v) MYC, FGFR1, ERG, and MDM2. When a combination of probes consisting of MYC and FGFR1 is used, a MYC % gain (% gain is % of cells with MYC copy numbers >2) of greater than or equal to 26 and/or a FGFR1% loss (% loss is % of cells with FGFR1 copy numbers <2) of greater than or equal to 26 indicates that the patient has a high risk of developing aggressive, prostate adenocarcinoma. When a combination of probes comprising (or consisting of) MYC, FGFR1, and ERG is used, a MYC % gain (% gain is % of cells with MYC copy numbers >2) of greater than or equal to 14, a FGFR1% loss (% loss is % of cells with FGFR1 copy numbers <2) of greater than or equal to 26, and/or an ERG % 2+Edel of greater than or equal to 10 indicates that the patient has a high risk of developing aggressive, prostate adenocarcinoma. When a combination of probes comprising (or consisting of) MYC, FGFR1, ERG, and PTEN is used, a MYC % gain (% gain is % of cells with MYC copy numbers >2) of greater than or equal to eight, a FGFR1% loss (% loss is % of cells with FGFR1 copy numbers <2) of greater than or equal to 26, an ERG % 2+Edel of greater than or equal to 10, and/or a PTEN % homozygous loss of greater than or equal to 20 indicates that the patient has a high risk of developing aggressive, prostate adenocarcinoma. When a combination of probes comprising (or consisting of) MYC, FGFR1, ERG, and MYCN is used, a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MYCN % gain (% gain is % of cells with MYCN copy numbers >2) of greater than or equal to 20 indicates that the patient has a high risk of developing aggressive, prostate adenocarcinoma. When a combination of probes comprising (or consisting of) MYC, FGFR1, ERG, and MDM2 is used, a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MDM2% gain (% gain is % of cells with MDM2 copy numbers >2) of greater than or equal to 10 indicates that the patient has a high risk of developing aggressive, prostate adenocarcinoma. The probe set of (i) can further consist of, or any of the probe sets of (ii)-(v) can further comprise, one or more of a chromosome enumeration probe for chromosome 8, a chromosome enumeration probe for chromosome 10, a locus-specific probe for AURKA, a locus-specific probe for NKX3.1, a locus-specific probe for P27, a break-apart probe for ETV1, and one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired.

The method can further comprise obtaining a clinical parameter, such as a clinical parameter selected from the group consisting of a Gleason score, a tumor stage, a level of PSA, a nomogram, methylation status, mutation, and age of the patient, any of which can be combined with the determination of the presence of chromosomal abnormalities for prognosis. The above method can further comprise monitoring a patient identified as having aggressive, prostatic adenocarcinoma during treatment by repeating (a) and (b) over a course of treatment. If the patient has already undergone a radical prostatectomy, the treatment can be an adjuvant treatment. With regard to the above methods, the patient may have already been identified as having aggressive, prostatic adenocarcinoma by another method, such as a method selected from the group consisting of a histological examination of a sample of prostate cells, a method of detecting/screening a sample of urine for a marker of aggressive, prostatic adenocarcinoma, and a method of detecting/screening a sample of blood for a marker of aggressive, prostatic adenocarcinoma.

A method of identifying a patient with indolent, prostatic adenocarcinoma is also provided. The method comprises (or consists of) (a) contacting a sample from the patient with a set of detectably labeled probes comprising two, three, four, five or six probes selected from the group consisting of a locus-specific probe for MYC, a locus-specific probe for FGFR1, a break-apart probe for ERG, a locus-specific probe for PTEN, a locus-specific probe for MYCN, and a locus-specific probe for MDM2 under hybridizing conditions and (b) determining the presence of chromosomal abnormalities in the sample. Examples of combinations of probes include, but are not limited to, (i) MYC and FGFR1, (ii) MYC, FGFR1, and ERG, (iii) MYC, FGFR1, ERG, and PTEN, (iv) MYC, FGFR1, ERG, and MYCN, and (v) MYC, FGFR1, ERG, and MDM2. When a combination of probes consisting of MYC and FGFR1 is used, a MYC % gain (% gain is % of cells with MYC copy numbers >2) of greater than or equal to two and/or a FGFR1% loss (% loss is % of cells with FGFR1 copy numbers <2) of greater than or equal to 10 indicates that the patient has a high risk of developing aggressive, prostate adenocarcinoma. When a combination of probes comprising (or consisting of) MYC, FGFR1, and ERG is used, a MYC % gain (% gain is % of cells with MYC copy numbers >2) of greater than or equal to two, a FGFR1% loss (% loss is % of cells with FGFR1 copy numbers <2) of greater than or equal to 10, and/or an ERG % 2+Edel of greater than or equal to two indicates that the patient has a high risk of developing aggressive, prostate adenocarcinoma. When a combination of probes comprising (or consisting of) MYC, FGFR1, ERG, and PTEN is used, a MYC % gain (% gain is % of cells with MYC copy numbers >2) of greater than or equal to two, a FGFR1% loss (% loss is % of cells with FGFR1 copy numbers <2) of greater than or equal to 10, an ERG % 2+Edel of greater than or equal to 10, and/or a PTEN % homozygous loss of greater than or equal to 20 indicates that the patient has a high risk of developing aggressive, prostate adenocarcinoma. When a combination of probes comprising (or consisting of) MYC, FGFR1, ERG, and MYCN is used, a MYC % gain (% gain is % of cells with MYC copy numbers >2) of greater than or equal to two, a FGFR1% loss (% loss is % of cells with FGFR1 copy numbers <2) of greater than or equal to 18, an ERG % 2+Edel of greater than or equal to two, and/or a MYCN % gain (% gain is % of cells with MYCN copy numbers >2) of greater than or equal to 20 indicates that the patient has a high risk of developing aggressive, prostate adenocarcinoma. When a combination of probes comprising (or consisting of) MYC, FGFR1, ERG, and MDM2 is used, a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to two, and/or a MDM2% gain (% gain is % of cells with MDM2 copy numbers >2) of greater than or equal to three indicates that the patient has a high risk of developing aggressive, prostate adenocarcinoma, and none of the foregoing indicates that the patient has indolent, prostatic adenocarcinoma. The probe set of (i) can further consist of, or any of the probe sets of (ii)-(v) can further comprise, a chromosome enumeration probe for chromosome 8, a chromosome enumeration probe for chromosome 10, a locus-specific probe for AURKA, a locus-specific probe for NKX3.1, a locus-specific probe for P27, a locus-specific probe for MDM2, a locus-specific probe for MYCN, a break-apart probe for ETV1, and/or one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired.

The method can further comprise obtaining a clinical parameter, such as a clinical parameter selected from the group consisting of a Gleason score, a tumor stage, a level of PSA, a nomogram, methylation status, mutation, and age of the patient, any of which can be combined with the determination of the presence of chromosomal abnormalities for prognosis. The above method can further comprise monitoring a patient identified as having aggressive, prostatic adenocarcinoma during treatment by repeating (a) and (b) over a course of treatment. Alternatively, the above methods can further comprise surveilling a patient identified as having indolent, prostatic adenocarcinoma by repeating (a) and (b) periodically. With regard to the above methods, the patient may have already been identified as having aggressive or indolent, prostatic adenocarcinoma by another method, such as a method selected from the group consisting of a histological examination of a sample of prostate cells, a method of detecting/screening a sample of urine for a marker of aggressive or indolent, prostatic adenocarcinoma, and a method of detecting/screening a sample of blood for a marker of aggressive or indolent, prostatic adenocarcinoma.

The sample can be any suitable sample. Examples of suitable samples include, but are not limited to, histological specimens, sections of which can be mounted on slides. The specimen can be from a radical prostatectomy, a biopsy (e.g., needle biopsy), a transurethral resection of the prostate (TURP), and the like. The section can be formalin-fixed and paraffin-embedded (FFPE) and placed on a microscope slide. Alternatively, a section preserved by other means, such as freezing, can be used, or a cytology specimen, such as a blood sample, or a urine sample can be used.

If the patient just had a radical prostatectomy, in addition to using the removed prostate as a source of a sample of prostate cells, which can be used fresh or embedded in paraffin and fixed with formalin, another sample, such as blood or urine, can be used. If analysis of the sample in accordance with a method described herein reveals the presence of at least one chromosomal abnormality indicative of a high risk for aggressive, prostatic adenocarcinoma, e.g., recurrence, metastasis, and possibly even death from disease, it can be beneficial for the patient to receive immediate treatment to prevent, or inhibit, the progression of the disease, such as by adjuvant therapy.

If the patient is receiving, or has received, an initial diagnosis of prostate cancer, a sample, such as a sample obtained from a biopsy of the prostate, blood, or urine, can be used. If analysis of the sample in accordance with a method described herein reveals the presence of at least one chromosomal abnormality indicative of a high risk for aggressive, prostatic adenocarcinoma, it can be beneficial for the patient to receive immediately a radical prostatectomy, alone or in further combination with one or more other treatments. Alternatively, if analysis of the sample in accordance with a method described herein reveals no chromosomal abnormality, it can be beneficial for the patient to be monitored or undergo active surveillance.

With regard to all of the above methods, the nature/size of the probe will depend, at least in part, on the method used to determine a particular parameter, e.g., copy number, copy number ratio, or percentage gain of a gene of interest. When an above diagnostic/prognostic method is carried out by in situ hybridization, such as FISH, for example, the probe can be relatively large. When an above diagnostic/prognostic method is carried by another method, the probe can be smaller, even substantially smaller, than the probe used for in situ hybridization, such as FISH, in which case the probe preferably hybridizes to a sequence within the gene of interest.

In view of the above, a probe for detecting a parameter involving MYC, for example, such as the copy number of MYC (e.g., gain), a copy number ratio involving MYC (e.g., MYC/CEP8 gain), or the percentage gain of MYC, by in situ hybridization, such as FISH, preferably hybridizes to the q24 region of chromosome 8 (8q24), which comprises the MYC gene. The probe also can hybridize to an adjacent region located on the centromeric side of 8q24, an adjacent region located on the telomeric side of 8q24, or both. A preferred probe covers approximately 820 kb, such as 821 kb, of 8q24 and is centered on the MYC gene. A probe for detecting a parameter involving MYC by another method can be smaller, even substantially smaller, than the probe used for in situ hybridization, such as FISH, in which case the probe preferably hybridizes to a sequence within the MYC gene (sequence information is available online from sources such as GenBank (www.ncbi.nlm.nih.gov/genbank) and GeneCards® (www.genecards.org)). "MYC" is used herein to refer to any and all probes that can be used to determine a parameter involving MYC, whether copy number, copy number ratio, percentage gain, and the like, irrespective of the particular method used to determine the parameter.

A probe for detecting a parameter involving FGFR1, for example, such as the copy number of FGFR1 (e.g., loss or gain), a copy number ratio involving FGFR1 (e.g., FGFR1/CEP8 loss or FGFR1/CEP8 gain), or the percentage loss or gain of FGFR1, by in situ hybridization, such as FISH, preferably hybridizes to the p11-12 regions of chromosome 8 (8p11-12), which comprises the FGFR1 gene. The probe also can hybridize to an adjacent region located on the centromeric side of 8p11-12, an adjacent region located on the telomeric side of 8p11-12, or both. A preferred probe covers approximately 530 kb, such as 531 kb, of 8p12 and is centered on the FGFR1 gene. A probe for detecting a parameter involving FGFR1 by another method can be smaller, even substantially smaller, than the probe used for in situ hybridization, such as FISH, in which case the probe preferably hybridizes to a sequence within the FGFR1 gene (sequence information is available online from sources such as GenBank (www.ncbi.nlm.nih.gov/genbank) and GeneCards® (www.genecards.org)). "FGFR1" may be used herein to refer to any and all probes that can be used to determine a parameter involving FGFR1, whether copy number, copy number ratio, percentage gain, and the like, irrespective of the particular method used to determine the parameter.

A probe for detecting a parameter involving PTEN, for example, such as the copy number of PTEN (e.g., PTEN loss or PTEN homozygous loss), a copy number ratio involving PTEN (e.g., PTEN/CEP10 loss), or the percentage loss of PTEN, by in situ hybridization, such as FISH, preferably hybridizes to the q23 region of chromosome 10 (10q23.31), which comprises part of the PTEN gene and an adjacent region located on the telomeric side of 10q23. A preferred PTEN probe covers approximately 340-350 kb, such as 344 kb, of 10q23.31. Adjacent regions of the PTEN gene probe include STS markers D10S215 on the centromeric side and SHGC-77962 on the telomeric side. A probe for detecting a parameter involving PTEN by another method can be smaller, even substantially smaller, than the probe used for in situ hybridization, such as FISH, in which case the probe preferably hybridizes to a sequence within the PTEN gene or an adjacent region of the PTEN gene (sequence information is available online from sources such as GenBank (www.ncbi.nlm.nih.gov/genbank) and GeneCards® (www.genecards.org)). "PTEN" may be used herein to refer to any and all probes that can be used to determine a parameter involving PTEN, whether copy number, copy number ratio, percentage homozygosity, and the like, irrespective of the particular method used to determine the parameter.

A probe for detecting a parameter involving ERG, for example, such as a rearrangement, alone or in further combination with interstitial chromosomal deletions 5' to the ERG gene, e.g., percentage 2+Edel, by in situ hybridization, such as FISH, preferably hybridizes to the q22 region of chromosome 21 (21q22), which comprises the ERG gene. A preferred ERG probe is a break-apart probe, i.e., a pair of probes, one of which is telomeric and the other of which is centromeric to the ERG gene, and detects rearrangements involving the ERG gene and adjacent chromosomal deletions. A probe for detecting a parameter involving ERG by another method can be smaller, even substantially smaller, than the probe used for in situ hybridization, such as FISH, in which case the probe preferably hybridizes to a sequence within the ERG gene (sequence information is available online from sources such as GenBank (www.ncbi.nlm.nih.gov/genbank) and GeneCards® (www.genecards.org)). "ERG" may be used herein to refer to any and all probes that can be used to determine a parameter involving ERG, whether a rearrangement, e.g., 2+Edel, and the like, irrespective of the particular method used to determine the parameter.

A chromosome enumeration probe for detecting a parameter involving chromosome 8, such as the copy number of chromosome 8 (e.g., gain or loss) or a copy number ratio involving a gene (i.e., a gene on chromosome 8) and chromosome 8 (e.g., FGFR1/CEP8 gain or FGFR1/CEP8 loss), by in situ hybridization, such as FISH, preferably hybridizes to the α-satellite DNA in the region of 8p11.1-q11.1 at the centromere of chromosome 8. Alternatively, the chromosome enumeration probe can hybridize to an arm of chromosome 8, provided that the probe accurately represents the status of chromosome 8 with regard to copy number gain or copy number loss.

A chromosome enumeration probe for detecting a parameter involving chromosome 10, such as the copy number of chromosome 10 (e.g., loss) or a copy number ratio involving a gene (i.e., a gene on chromosome 10) and chromosome 10 (e.g., PTEN/CEP10 loss), by in situ hybridization, such as FISH, preferably hybridizes to the a-satellite DNA in the region of 10p11.1-q11.1 at the centromere of chromosome 10. Alternatively, the chromosome enumeration probe can hybridize to an arm of chromosome 10, provided that the probe accurately represents the status of chromosome 10 with regard to copy number gain or copy number loss.

A probe for detecting a parameter involving AURKA, such as the copy number of AURKA (e.g., AURKA gain), a copy number ratio involving AURKA, or the percentage gain of AURKA, by in situ hybridization, such as FISH, preferably hybridizes to the q13 region of chromosome 20 (20q13), which comprises the AURKA gene. The probe also can hybridize to an adjacent region located on the centromeric side of 20q13, an adjacent region located on the telomeric side of 20q13, or both. A preferred probe covers approximately 638 kb-858 kb, such as 648 kb, of 20q13 and is centered on the AURKA gene. A probe for detecting a parameter involving AURKA by another method can be smaller, even substantially smaller, than the probe used for in situ hybridization, such as FISH, in which case the probe preferably hybridizes to a sequence within the AURKA gene (sequence information is available online from sources such as GenBank (www.ncbi.nlm.nih.gov/genbank) and GeneCards® (www.genecards.org)). "AURKA" is used herein to refer to any and all probes that can be used to determine a parameter involving AURKA, whether copy number, copy number ratio, percentage gain, and the like, irrespective of the particular method used to determine the parameter.

A probe for detecting a parameter involving NKX3.1, such as the copy number of NKX3.1 (e.g., NKX3.1 loss), a copy number ratio involving NKX3.1, or the percentage loss of NKX3.1, by in situ hybridization, such as FISH, preferably hybridizes to the p21 region of chromosome 8 (8p21), which comprises the NKX3.1 gene. The probe also can hybridize to an adjacent region located on the centromeric side of 8p21, an adjacent region located on the telomeric side of 8p21, or both. A preferred probe covers approximately 518-538 kb, such as 528 kb, of 8p21 and is centered on the NKX3.1 gene. A probe for detecting a parameter involving NKX3.1 by another method can be smaller, even substantially smaller, than the probe used for in situ hybridization, such as FISH, in which case the probe preferably hybridizes to a sequence within the NKX3.1 gene (sequence information is available online from sources such as GenBank (www.ncbi.nlm.nih.gov/genbank) and GeneCards® (www.genecards.org)). "NKX3.1" is used herein to refer to any and all probes that can be used to determine a parameter involving NKX3.1, whether copy number, copy number ratio, percentage gain, and the like, irrespective of the particular method used to determine the parameter.

A probe for detecting a parameter involving P27, such as the copy number of P27 (e.g., P27 loss), a copy number ratio involving P27, or the percentage loss of P27, by in situ hybridization, such as FISH, preferably hybridizes to the p13-12 region of chromosome 12 (12p13-12), which comprises the P27 gene. The probe also can hybridize to an adjacent region located on the centromeric side of 12p13-12, an adjacent region located on the telomeric side of 12p13-12, or both. A preferred probe covers approximately 382-412 kb, such as 392 kb, of 12p13-12 and is centered on the P27 gene. A probe for detecting a parameter involving P27 by another method can be smaller, even substantially smaller, than the probe used for in situ hybridization, such as FISH, in which case the probe preferably hybridizes to a sequence within the P27 gene (sequence information is available online from sources such as GenBank (www.ncbi.nlm.nih.gov/genbank) and GeneCards® (www.genecards.org)). "P27" is used herein to refer to any and all probes that can be used to determine a parameter involving P27, whether copy number, copy number ratio, percentage gain, and the like, irrespective of the particular method used to determine the parameter.

A probe for detecting a parameter involving MDM2, such as the copy number of MDM2 (e.g., MDM2 gain), a copy number ratio involving MDM2, or the percentage gain of MDM2, by in situ hybridization, such as FISH, preferably hybridizes to the q15 region of chromosome 12 (12q15), which comprises the MDM2 gene. The probe also can hybridize to an adjacent region located on the centromeric side of 12q15, an adjacent region located on the telomeric side of 12q15, or both. A preferred probe covers approximately 210 kb, such as 209 kb, of 12q15 and is centered on the MDM2 gene. A probe for detecting a parameter involving MDM2 by another method can be smaller, even substantially smaller, than the probe used for in situ hybridization, such as FISH, in which case the probe preferably hybridizes to a sequence within the MDM2 gene (sequence information is available online from sources such as GenBank (www.ncbi.nlm.nih.gov/genbank) and GeneCards® (www.genecards.org)). "MDM2" is used herein to refer to any and all probes that can be used to determine a parameter involving MDM2, whether copy number, copy number ratio, percentage gain, and the like, irrespective of the particular method used to determine the parameter.

A probe for detecting a parameter involving MYCN, such as the copy number of MYCN (e.g., MYCN gain), a copy number ratio involving MYCN, or the percentage gain of MYCN, by in situ hybridization, such as FISH, preferably hybridizes to the p24 region of chromosome 2 (2p24), which comprises the MYCN gene. The probe also can hybridize to an adjacent region located on the centromeric side of 2p24, an adjacent region located on the telomeric side of 2p24, or both. A preferred probe covers approximately 195-205 kb, such as 200 kb, of 2p24 and is centered on the MYCN gene. A probe for detecting a parameter involving MYCN by another method can be smaller, even substantially smaller, than the probe used for in situ hybridization, such as FISH, in which case the probe preferably hybridizes to a sequence within the MYCN gene (sequence information is available online from sources such as GenBank (www.ncbi.nlm.nih.gov/genbank) and GeneCards® (www.genecards.org)). "MYCN" is used herein to refer to any and all probes that can be used to determine a parameter involving MYCN, whether copy number, copy number ratio, percentage gain, and the like, irrespective of the particular method used to determine the parameter.

A probe for detecting a parameter involving ETV1, for example, such as a rearrangement, by in situ hybridization, such as FISH, preferably hybridizes to the p21 region of chromosome 7 (7p21), which comprises the ETV1 gene. A preferred ETV1 probe is a break-apart probe, i.e., a pair of probes, one of which is telomeric and the other of which is centromeric to the ETV1 gene, and detects rearrangements involving the ETV1 gene and adjacent chromosome deletions. A probe for detecting a parameter involving ETV1 by another method can be smaller, even substantially smaller, than the probe used for in situ hybridization, such as FISH, in which case the probe preferably hybridizes to a sequence within the ETV1 gene (sequence information is available online from sources such as GenBank (www.ncbi.nlm.nih.gov/genbank) and GeneCards® (www.genecards.org)). "ETV1" may be used herein to refer to any and all probes that can be used to determine a parameter involving ETV1, whether a rearrangement and the like, irrespective of the particular method used to determine the parameter.

The usage of probes as explained above applies to methods, probes and kits discussed herein. Descriptions of probes as set forth in the beginning of the "Detailed Description" also applies to methods, probes, and kits discussed herein.

The above method can be carried out using any suitable detection method known in the art. Preferably, the above method is carried out using in situ hybridization, such as fluorescent in situ hybridization (FISH). Preferably, each probe is detectably labeled with a distinct label, such as a distinct fluorophore. Alternatively, radiolabeled nucleotide detection (in situ hybridization (ISH)), chromomeric hybridization detection, and the like, as described herein, can be used.

When the above methods are carried out by in situ hybridization, in which each probe is detectably labeled with a distinct label, such as by FISH, in which each probe is labeled with a distinct fluorophore, the methods can be carried out on a sample of prostate cells, which are fresh, such as fresh cells from a biopsy of the prostate (fresh cells can be cultured for 1-3 days and a blocker, such as Colcemid, can be added to the culture to block the cells in metaphase, during which chromosomes are highly condensed and can be visualized), frozen, or fixed (e.g., fixed in formalin and embedded in paraffin), treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a cell suspension can be applied as a single layer onto a slide, and the cell density can be measured by a light or phase contrast microscope. Cells also can be obtained from other sources, such as bodily fluids, e.g., urine or semen, preserved in fixatives, such as methanol-acetic acid (Carnoy's reagent), and applied to a slide or similar support for microscopic examination and analysis.

FFPE histological specimens slides (sections) can be baked at about 56-60° C. for around 2-24 hrs, then pretreated two to three times in Hemo-De (Scientific Safety Solvents) or Xyline for about 5-10 minutes each at room temperature, rinsed twice in 100% ethanol for about one minute each at room temperature. Slides then can be incubated in pre-treatment solution (1×SSC, pH 7.0) at around 75-85° C. for about 35-50 minutes, rinsed for about three minutes in deionized water, incubated for about 17-27 minutes in 0.15% pepsin in 0.1N HCl solution at around 37° C., and rinsed again for about three minutes in deionized water. Slides can be dehydrated for one minute each in 70%, 85%, and 100% ethanol and then air dried. Ten microliters of a probe hybridization mix (LSI® buffer, blocking DNA, labeled probes) can be added to separate specimen slides, and coverslips can be applied and sealed with rubber cement. Slides can be co-denatured for about five minutes at around 71-75° C. and hybridized for about 4-24 hours at around 37° C. on a ThermoBrite (Abbott Molecular, Inc., Des Plaines, Ill.). Following hybridization, the rubber cement can be peeled off, and coverslips can be removed by soaking in 1×SSC, pH 7.0, for about 3-5 minutes. Then the slides can be placed in a wash solution of 2×SSC/0.3% NP-40 preheated at around 73° C. for about 2-5 minutes. Then the slides can be put in 1×SSC, pH 7.0, for about one minute as a final rinse. Then the supports carrying the samples can be either counterstained with a nuclear DNA-binding stain, such as 4',6-diamidino-2-phenylindole (DAPI) either in solution, or upon drying the sample in the dark. In the latter case, the samples are counterstained with about 10 μL DAPI, and new coverslips are placed over the samples. The samples can then be viewed or stored, e.g., at about −20° C.

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed.

An area evidencing some level of dysplasia or a suspicious lesion can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, about 3-10 abnormal areas are selected and, within each abnormal area, 10 random nuclei are analyzed under high power (64× or 100× objective). Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

Thus, such methods comprise contacting a sample obtained from a patient, e.g., a sample of prostate cells, blood urine, or nucleic acids, with a set of detectably labeled probes as described above under hybridizing conditions. Hybridizing conditions allow (or promote) the probes to bind selectively with their target nucleic acid sequences and form stable hybridization complexes. Such methods further comprise detecting the formation of the hybridization complexes and counting the number of hybridization complexes. In view of the number of hybridization complexes the method further comprises determining the number of copies of one or more chromosomal abnormalities. A copy number of a chromosomal abnormality can be compared to a pre-determined cut-off, such as a cut-off within a range provided herein or a specific cut-off provided herein, wherein a copy number greater than the pre-determined cut-off (i.e., for a gain) or a copy number less than the pre-determined cut-off (i.e., for a loss), as appropriate, indicates that a patient does or does not have aggressive/indolent prostate cancer as described herein.

While deparaffinization, pretreatment, staining, and routine slide washing also can be conducted in accordance with methods known in the art, use of an automated system, however, such as the VP 2000 Process (Abbott Molecular, Inc., Des Plaines, Ill.), decreases the amount of time needed to prepare slides for evaluation. Slides can be prepared in large batches (e.g., 50 slides), as opposed to small batches (e.g., 4 slides) when standard Coplin jars are used for post-hybridization washing. In addition, the scoring of slides can be fully automated using automated imaging, thereby reducing the amount of hands-on time required for specimen analysis. Full automation also enables signal enumeration and subsequent data analysis using an imaging algorithm that captures more abnormal cells more frequently and consistently.

Other methods already known in the art or currently under development may require or prefer the use of a sample of prostate cells that is other than cells fixed in formalin and embedded in paraffin, e.g., fresh or frozen cells, homogenized cells, lysed cells, or isolated or purified nucleic acids (e.g., a "nucleic acid sample" such as DNA) from prostate cells ("sample of prostate cells" as used herein is intended to encompass all forms of a sample of prostate cells that enable the determination of copy number and gain/loss). Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dH-PLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step can precede contact of the probes with the targets. Alternatively, the probe and the target can be subjected to denaturing conditions together while in contact with one another, or with subsequent contact of the probe with the biological sample. Hybridization can be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, a blocking agent, such as unlabeled blocking nucleic acid, as described in U.S. Pat. No. 5,756,696 (the contents of which are herein incorporated by reference in their entirety, and specifically for the description of the use of blocking nucleic acid), can be used. Other conditions can be readily employed for specifically hybridizing the probes to their nucleic acid targets present in the sample, as would be readily apparent to one of skill in the art. Hybridization protocols are described, for example, in Pinket et al., PNAS USA 85: 9138-9142 (1988); In situ Hybridization Protocols, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA can be removed by a series of washes. Temperature and salt concentrations are suitably chosen for a desired stringency. The level of stringency required depends on the complexity of a specific probe sequence in relation to the genomic sequence, and can be determined by systematically hybridizing probes to samples of known genetic composition. In general, high stringency washes can be carried out at a temperature in the range of about 65 to about 80° C. with about 0.2× to about 2×SSC and about 0.1% to about 1% of a non-ionic detergent, such as Nonidet P-40 (NP40). If lower stringency washes are required, the washes can be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method can be used in conjunction with the methods described herein for observing multiple fluorophores. In the case where fluorescence microscopy is employed, hybridized samples can be viewed under light suitable for excitation of each fluorophore and with the use of an appropriate filter or filters. Automated digital imaging systems, such as the MetaSystems, BioView or Applied Imaging systems, alternatively can be used, along with signal enumeration and data acquisition algorithms.

Depending on the method employed, a digital image analysis system can be used to facilitate the display of results and to improve the sensitivity of detecting small differences in fluorescence intensity. An exemplary system is BioView automated slide scanner with image analysis software. Another exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display, which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

The above methods can be used to stratify patients into those who need aggressive treatment (e.g., surgery, hormone therapy, radiation, or, if post-surgery (e.g., simple or radical prostatectomy), adjuvant treatment (e.g., androgen deprivation)), and those who do not need aggressive treatment, such as those who should undergo active surveillance or watchful waiting. The methods also can be used to monitor the progression or recurrence of prostate cancer, to determine the candidacy of a patient for treatment, and to monitor the efficacy of prophylactic or therapeutic treatment (e.g., hormone or radiation therapy) of prostate cancer. Results obtained with urine- or blood-based detection methods can be confirmed with the above methods.

Additionally, provided herein is method of monitoring the progression of prostate cancer in a subject. Optimally, the method comprises the steps of:

(a) determining chromosomal abnormalities in a sample from a subject;

(b) determining the levels of chromosomal abnormalities in a later sample from the subject; and (c) comparing the levels of chromosomal abnormalities as determined in step (b) with the levels of chromosomal abnormalities as determined in step (a), wherein if the levels in step (b) are unchanged or unfavorable when compared to the levels determined in step (a), then prostate cancer is determined to have continued, progressed or worsened in the subject. By comparison, if the levels as determined in step (b) are favorable when compared to the levels as determined in step (a), then prostate cancer is determined to have discontinued, regressed or improved in the subject.

Optionally, the method further comprises comparing the levels of chromosomal abnormalities as determined in step (b), for example, with predetermined levels. Further, optionally the method comprises treating the subject, e.g., with one or more pharmaceutical compositions, radiation, and/or hormone therapy, for a period of time if the comparison shows that the levels as determined in step (b), for example, are unfavorably altered with respect to the predetermined levels.

Thus, the method can further comprise prognosticating or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a sample of prostate cells for chromosomal abnormalities. Generally, in making such a comparison, the predetermined level is obtained by running a particular assay a sufficient number of times and under appropriate conditions such that a linkage or association of a particular chromosomal abnormality (presence or level) with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the chromosomal abnormality (presence or level) may be "unchanged," "favorable" (or "favorably altered"), or "unfavorable" (or "unfavorably altered"). "Elevated" or "increased" refers to a level of chromosomal abnormality in a sample of prostate cells that is higher than a typical or normal level or range (e.g., predetermined level), or is higher than another reference level or range (e.g., earlier or baseline sample). The term "lowered" or "reduced" refers to a level of chromosomal abnormality in a sample of prostate cells that is lower than a typical or normal level or range (e.g., predetermined level), or is lower than another reference level or range (e.g., earlier or baseline sample). The term "altered" refers to a level of chromosomal abnormality in a sample of prostate cells that is altered (increased or decreased) over a typical or normal level or range (e.g., predetermined level), or over another reference level or range (e.g., earlier or baseline sample). The typical or normal level or range for a given chromosomal abnormality is defined in accordance with standard practice.

Moreover, the present disclosure also relates to methods of determining whether a subject predisposed to or suffering from prostate cancer will benefit from treatment. In particular, the disclosure relates to companion diagnostic methods and products. Thus, the method can further encompass selecting or identifying candidates for therapy.

Thus, in particular embodiments, the disclosure also provides a method of determining whether a subject having, or at risk for, prostate cancer is a candidate for therapy. Generally, the subject is one who has experienced some symptom of the disease or who has actually been diagnosed as having, or being at risk for, such a disease, and/or who demonstrates unfavorable levels of chromosomal abnormalities, as described herein.

The method optionally comprises an assay as described herein, where levels of chromosomal abnormalities are assessed before and following treatment of a subject. The observation of unfavorable levels of chromosomal abnormalities following treatment confirms that the subject will not benefit from receiving further or continued treatment, whereas the observation of favorable levels of chromosomal abnormalities following treatment confirms that the subject will benefit from receiving further or continued treatment. This confirmation assists with management of clinical studies, and provision of improved patient care.

Probes

A set of detectably labeled probes is provided. The set of probes is:

(i) a set of detectably labeled probes consisting of a locus-specific probe for MYC and a locus-specific probe for FGFR1, (ii) a set of detectably labeled probes comprising a locus-specific probe for MYC, a locus-specific probe for FGFR1, a break-apart probe for ERG, and a locus-specific probe for NKX3.1, (iii) a set of detectably labeled probes comprising a locus-specific probe for MYC, a break-apart probe for ETV1, a locus-specific probe for FGFR1, and a locus-specific probe for P27, (iv) a set of detectably labeled probes comprising a locus-specific probe for MYC, a locus-specific probe for FGFR1, a locus-specific probe for PTEN, and a chromosome enumeration probe for chromosome 8, (v) a set of detectably labeled probes comprising a chromosome enumeration probe for chromosome 8, a locus-specific probe for MYC, a break-part probe for ERG, and a locus-specific probe for FGFR1, (vi) a set of detectably labeled probes comprising a chromosome enumeration probe for chromosome 8, a locus-specific probe for MYC, a break-apart probe for ERG, and a locus-specific probe for NKX3.1, (vii) a set of detectably labeled probes comprising a chromosome enumeration probe for chromosome 8, a locus-specific probe for MYC, a break-apart probe for ERG, and a locus-specific probe for FGFR1, (viii) a set of detectably labeled probes comprising a chromosome enumeration probe for chromosome 8, a locus-specific probe for MYC, a break-apart probe for ERG, and a locus-specific probe for MYCN, (ix) a set of detectably labeled probes comprising a chromosome enumeration probe for chromosome 8, a locus-specific probe for MYC, a break-apart probe for ERG, and a locus-specific probe for MDM2, (x) a set of detectably labeled probes comprising a chromosome enumeration probe for chromosome 8, a locus-specific probe for MYC, a break-apart probe for ETV1, and a locus-specific probe for FGFR1, (xi) a set of detectably labeled probes comprising a locus-specific probe for AURKA, a locus-specific probe for MYC, a break-apart probe for ERG, and a locus-specific probe for FGFR1, (xii) a set of detectably labeled probes comprising a chromosome enumeration probe for chromosome 8, a locus-specific probe for MYC, a break-apart probe for ERG, and a locus-specific probe for PTEN, (xiii) a set of detectably labeled probes comprising a locus-specific probe for MYC, a break-apart probe for ERG, a locus-specific probe for FGFR1, and a locus-specific probe for P27, or (xiv) a set of detectably labeled probes comprising a locus-specific probe for AURKA, a chromosome enumeration probe for chromosome 8, a locus-specific probe for MYC, and a break-apart probe for ERG.

In another embodiment, the set of probes comprises (or consists of) a detectably labeled, locus-specific probe for MYC, a detectably labeled, locus-specific probe for FGFR1, and a detectably labeled, break-apart probe for ERG. The set of probes can further comprise a detectably labeled, locus-specific probe for PTEN, a detectably labeled, locus-specific probe for MYCN, a detectably labeled, locus-specific probe for MDM2, a detectably labeled chromosome enumeration probe for chromosome 8, a detectably labeled chromosome enumeration probe for chromosome 10, a detectably labeled locus-specific probe for AURKA, a detectably labeled locus-specific probe for NKX3.1, a detectably labeled locus-specific probe for P27, a detectably labeled break-apart probe for ETV1, and one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired.

An example of a MYC probe is LSI MYC SPECTRUMAQUA™ Probe, which is approximately 821 kb in length, and is available from Abbott Molecular, Inc. A smaller MYC probe, which is approximately 120 kb in length, also is available from Abbott Molecular. Inc. as LSI C-MYC SPECTRUMORANGE™ Probe.

An example of a FGFR1 probe is LSI FGFR1 SPECTRUMRED™ Probe, which is approximately 531 kb in length and available from Abbott Molecular, Inc.

An example of an ERG probe is an ERG Cen probe, which is 209 kb in length. Another example of an ERG probe is an ERG Tel probe, which is 561 kb in length. Both probes are available from Abbott Molecular, Inc.

An example of a PTEN probe is LSI PTEN SPECTRUMORANGE™ Probe, which is approximately 344 kb in length. and is available from Abbott Molecular, Inc Another example of a PTEN probe is LSI PTEN SPECTRUMGOLD™ Probe, which is approximately 344 kb in length and available from Abbott Molecular, Inc.

A MYCN probe, which is 200 kb in length, is available from Abbott Molecular, Inc.

An example of a MDM2 probe is LSI MDM2 SPECTRUMORANGE™ probe, which is approximately 209 kb in length and available from Abbott Molecular, Inc.

An example of a chromosome enumeration probe for chromosome 8 is CEP8® SPECTRUMAQUA™, which is available from Abbott Molecular, Inc. CEP8® hybridizes to a-satellite DNA in the region of 8p11.1-q11.1 at the centromere of chromosome 8.

An example of a chromosome enumeration probe for chromosome 10 is CEP10t SPECTRUMGREEN™, which is available from Abbott Molecular, Inc. CEP10® hybridizes to α-satellite DNA in the region of 10p11.1-q11.1 at the centromere of chromosome 10.

An AURKA probe, which is 648 kb in length, is available from Abbott Molecular, Inc.

A NKX3.1 probe, which is 528 kb in length, is available from Abbott Molecular, Inc.

A P27 probe, which is 392 kb in length, is available from Abbott Molecular, Inc.

Examples of ETV1 probes include LSI ETV1 (Cen) SPECTRUMGREEN™ Probe, which is approximately 605 kb in length and hybridizes 5' to the ETV1 gene, and LSI ETV1 (Tel) SPECTRUMRED™ Probe, which is approximately 560 kb in length and hybridizes 3' to the ETV1 gene. Both probes are available from Abbott Molecular, Inc.

Chromosome enumerator probes (CEP) and locus-specific probes that target a chromosome region or subregion can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. In another embodiment, the chromosomal probes can be oligo probes. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., MYC.

The probes can be prepared by any method known in the art. Probes can be synthesized or recombinantly produced. Such probes can range in length from about 25,000 base pairs to about 800,000 base pairs.

Preferably, probes are detectably labeled, and each probe is distinctly labeled. Preferably, probes are detectably labeled, and each probe is distinctly labeled.

Preferably, the probes are detectably labeled with fluorophores, and each probe is distinctly labeled. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, SPECTRUMRED™ (Abbott Molecular, Inc.), SPECTRUMGOLD™ (Abbott Molecular, Inc.), SPECTRUMGREEN™ (Abbott Molecular, Inc.), SPECTRUMAQUA™ (Abbott Molecular, Inc.), TEXAS RED™ (Molecular Probes, Inc.), Lucifer yellow, and CASCADE BLUE™ acetylazide (Molecular Probes, Inc.). The particular label used is not critical; desirably, however, the particular label does not interfere with in situ hybridization of the probe and the detection of label on any other probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, end labeling, direct labeling by chemical modification of particular residues, such as cytosine residues (U.S. Pat. No. 5,491,224), and the like. Alternatively, the fluorophore can be covalently attached to nucleotides with activated linker arms, which have been incorporated into the probe, for example, via a linker to the deoxycytidine nucleotides of the probe that have been transaminated. Methods for labeling probes are described in U.S. Pat. No. 5,491,224, and Morrison et al., Molecular Cytogenetics: Protocols and Applications, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label-containing moieties. Agents that are detectable with visible light include cyanin dyes. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions alternatively can be visualized by enzymatic reactions of label moieties with suitable substrates for the production of insoluble color products. Each probe can be discriminated from other probes within the set by choice of a distinct label moiety. A biotin-containing probe within a set can be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kits

A kit is also provided. The kit comprises a set of probes, such as a set of probes as described above, which enables distinguishing between a patient with aggressive, prostatic adenocarcinoma and a patient with indolent, prostatic adenocarcinoma, and instructions for carrying out an above-described method. Alternatively, the kit comprises a set of probes, such as a set of probes as described above, that enables identification of a patient with a high risk of developing aggressive, prostatic adenocarcinoma or identification of a patient with indolent adenocarcinoma and instructions for carrying out an above-described method.

Thus, in one embodiment, the kit comprises (a) a set of probes, wherein the set of probes is (i) a set of detectably labeled probes consisting of a locus-specific probe for MYC and a locus-specific probe for FGFR1, (ii) a set of detectably labeled probes comprising a locus-specific probe for MYC, a locus-specific probe for FGFR1, and a break-apart probe for ERG, (iii) a set of detectably labeled probes comprising a locus-specific probe MYC, a locus-specific probe for FGFR1, a break-apart probe for ERG, and a locus-specific probe for PTEN, (iv) a set of detectably labeled probes comprising a locus-specific probe for MYC, a locus-specific probe for FGFR1, a break-apart probe for ERG, and a locus-specific probe for MYCN, (v) a set of detectably labeled probes comprising a locus-specific probe for MYC, a locus-specific probe for FGFR1, a break-apart probe for ERG, and a locus-specific probe for MDM2, (vi) a set of detectably labeled probes comprising a locus-specific probe for MYC, a locus-specific probe for FGFR1, a break-apart probe for ERG, and a locus-specific probe for NKX3.1, (vii) a set of detectably labeled probes comprising a locus-specific probe for MYC, a break-apart probe for ETV1, a locus-specific probe for FGFR1, and a locus-specific probe for P27, (viii) a set of detectably labeled probes comprising a locus-specific probe for MYC, a locus-specific probe for FGFR1, a locus-specific probe for PTEN, and a chromosome enumeration probe for chromosome 8 (CEP8), (ix) a set of detectably labeled probes comprising a chromosome enumeration probe for chromosome 8, a locus-specific probe for MYC, a break-part probe for ERG, and a locus-specific probe for FGFR1, (x) a set of detectably labeled probes comprising a chromosome enumeration probe for chromosome 8, a locus-specific probe for MYC, a break-apart probe for ERG, and a locus-specific probe for NKX3.1, (xi) a set of detectably labeled probes comprising a chromosome enumeration probe for chromosome 8, a locus-specific probe for MYC, a break-apart probe for ERG, and a locus-specific probe for FGFR1, (xii) a set of detectably labeled probes comprising a chromosome enumeration probe for chromosome 8, a locus-specific probe for MYC, a break-apart probe for ERG, and a locus-specific probe for MYCN, (xiii) a set of detectably labeled probes comprising a chromosome enumeration probe for chromosome 8, a locus-specific probe for MYC, a break-apart probe for ERG, and a locus-specific probe for MDM2, (xiv) a set of detectably labeled probes comprising a chromosome enumeration probe for chromosome 8, a locus-specific probe for MYC, a break-apart probe for ETV1, and a locus-specific probe for FGFR1, (xv) a set of detectably labeled probes comprising a locus-specific probe for AURKA, a locus-specific probe for MYC, a break-apart probe for ERG, and a locus-specific probe for FGFR1, (xvi) a set of detectably labeled probes comprising a chromosome enumeration probe for chromosome 8, a locus-specific probe for MYC, a break-apart probe for ERG, and a locus-specific probe for PTEN, (xvii) a set of detectably labeled probes comprising a locus-specific probe for MYC, a break-apart probe for ERG, a locus-specific probe for FGFR1, and a locus-specific probe for P27, or (xviii) a set of detectably labeled probes comprising a locus-specific probe for AURKA, a chromosome enumeration probe for chromosome 8, a locus-specific probe for MYC, and a break-apart probe for ERG. The locus-specific probe for FGFR1 in the sets of (i)-(vi), (viii), (xi), (xiv), (xv), and (xvii) is used to determine % loss of FGFR1, the locus-specific probe for FGFR1 in the sets of (vii), (ix), and, as an alternative to % loss of FGFR1, (xiv), is used to determine % gain of FGFR1, CEP8 in the sets of (ix)-(xiv), (xvi), and (xviii) is used to determine % loss of CEP8, the locus-specific probe for PTEN in sets (iii) and (viii) is used to determine % homozygous loss of PTEN, the locus-specific probe for PTEN in set (xvi) is used to determine % loss of PTEN, and the locus-specific probe for FGFR1 and CEP8 in the sets of (viii), and as an alternative to % gain of FGFR1, (ix), are used to determine % loss of FGFR1/CEP8 ratio. The kit further comprises (b) instructions for distinguishing between a patient with aggressive, prostatic adenocarcinoma and a patient with indolent, prostatic adenocarcinoma. The instructions comprise determining in a sample obtained from the patient the presence of chromosomal abnormalities. The method can comprise contacting the sample with a set of probes under hybridizing conditions, counting hybridization complexes, and comparing the number to a cut-off in a range of cut-offs or a specific cut-off as described herein. For example, a MYC % gain (% gain is % of cells with MYC copy numbers >2) of greater than or equal to two to less than or equal to 30, a FGFR1% loss (% loss is % of cells with FGFR copy numbers <2) of greater than or equal to 15 to less than or equal to 40, a FGFR1% gain (% gain is % of cells with FGFR copy numbers >2) of greater than or equal to two to less than or equal to 46, a CEP8% loss (% loss is % of cells with CEP8 copy numbers <2) of greater than or equal to 21 to less than or equal to 36, a CEP8% gain (% gain is % of cells with CEP8 copy numbers >2) of greater than or equal to 15 to less than or equal to 40, a FGFR1/CEP8% loss of greater than or equal to 13 to less than or equal to 72, a PTEN % homozygous loss (% homozygous loss is % of cells with PTEN copy numbers of zero) of greater than or equal to two and less than or equal to 40, a PTEN % loss (% loss is % of cells with PTEN copy number of less than two) of greater than or equal to 10 to less than or equal to 50, a ERG 2+Edel of greater than or equal to one to less than or equal to 30, a MYCN % gain (% gain is % of cells with MYCN copy numbers >2) of greater than or equal to two to less than or equal to 30, a MDM2% gain (% gain is % of cells with MDM2 copy numbers >2) of greater than or equal to two to less than or equal to 20, a NKX3.1% loss (% loss is % of cells with NKX3.1 copy numbers <2) of greater than or equal to 10 to less than or equal to 50, an ETV1% translocation/deletion of greater than or equal to 1 to less than or equal to 20, a P27% loss (% loss is % of cells with P27 copy numbers <2) of greater than or equal to 10 to less than or equal to 50, or an AURKA % gain (% gain is % of cells with AURKA copy numbers >2) of greater than or equal to 1 to less than or equal to 20 indicates that the patient has a high risk of developing aggressive, prostatic adenocarcinoma, whereas none of the above indicates that the patient has indolent, prostatic adenocarcinoma. If the patient has had a prostatectomy, the determination of the presence of a chromosomal abnormality in the sample indicates that the patient has a high risk of recurrence or metastasis, in which case the instructions can further comprise recommending that the patient consult his physician for immediate treatment to inhibit or prevent recurrence or metastasis. If the patient has/is being initially diagnosed with prostate cancer and the patient has a high risk of developing aggressive, prostatic adenocarcinoma, the instructions can further comprise recommending that the patient consult his physician for immediate treatment. If the patient has/is being initially diagnosed with prostate cancer and the patient has indolent, prostatic adenocarcinoma, the instructions can further comprise recommending active surveillance or watchful waiting.

In another embodiment, the kit comprises (a) a set of probes, wherein the set of probes is (i) a set of detectably labeled probes consisting of a locus-specific probe for MYC and a locus-specific probe for FGFR1, (ii) a set of detectably labeled probes comprising a locus-specific probe for MYC, a locus-specific probe for FGFR1, and a break-apart probe for ERG, (iii) a set of detectably labeled probes comprising a locus-specific probe MYC, a locus-specific probe for FGFR1, a break-apart probe for ERG, and a locus-specific probe for PTEN, (iv) a set of detectably labeled probes comprising a locus-specific probe for MYC, a locus-specific probe for FGFR1, a break-apart probe for ERG, and a locus-specific probe for MYCN, or (v) a set of detectably labeled probes comprising a locus-specific probe for MYC, a locus-specific probe for FGFR1, a break-apart probe for ERG, and a locus-specific probe for MDM2. Set (i) can further consist of, or the set of any of (ii)-(v) can further comprise, a chromosome enumeration probe for chromosome 8, a chromosome enumeration probe for chromosome 10, a locus-specific probe for AURKA, a locus-specific probe for NKX3.1, a locus-specific probe for P27, a break-apart probe for ETV1, and/or one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired. The kit further comprises (b) instructions for identifying a patient with a high risk of developing aggressive prostatic adenocarcinoma. The instructions comprise determining in a sample obtained from the patient the presence of chromosomal abnormalities. The method can comprise contacting the sample with a set of probes under hybridizing conditions, counting hybridization complexes, and comparing the number to a cut-off in a range of cut-offs or a specific cut-off as described herein. For example, for (i) a MYC % gain (% gain is % of cells with MYC copy numbers >2) of greater than or equal to 26 and/or a FGFR1% loss (% loss is % of cells with FGFR1 copy numbers <2) of greater than or equal to 26, for (ii) a MYC % gain (% gain is % of cells with MYC copy numbers >2) of greater than or equal to 14, a FGFR1% loss (% loss is % of cells with FGFR1 copy numbers <2) of greater than or equal to 26, and/or an ERG % 2+Edel of greater than or equal to 10, for (iii) a MYC % gain (% gain is % of cells with MYC copy numbers >2) of greater than or equal to eight, a FGFR1% loss (% loss is % of cells with FGFR1 copy numbers <2) of greater than or equal to 26, an ERG % 2+Edel of greater than or equal to 10, and/or a PTEN % homozygous loss of greater than or equal to 20, for (iv) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MYCN % gain (% gain is % of cells with MYCN copy numbers >2) of greater than or equal to 20, or for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MDM2% gain (% gain is % of cells with MDM2 copy numbers >2) of greater than or equal to 10 indicates that the patient has a high risk of developing aggressive, prostate adenocarcinoma. The instructions can further comprise instructions for obtaining a clinical parameter selected from the group consisting of a Gleason score, a tumor stage, a level of prostate-specific antigen (PSA), a nomogram, methylation status, mutation, and age of the patient, any of which can be combined with the determination of the presence of chromosomal abnormalities for prognosis.

In yet another embodiment, the kit comprises (a) a set of probes, wherein the set of probes is (i) a set of detectably labeled probes consisting of a locus-specific probe for MYC and a locus-specific probe for FGFR1, (ii) a set of detectably labeled probes comprising a locus-specific probe for MYC, a locus-specific probe for FGFR1, and a break-apart probe for ERG, (iii) a set of detectably labeled probes comprising a locus-specific probe MYC, a locus-specific probe for FGFR1, a break-apart probe for ERG, and a locus-specific probe for PTEN, (iv) a set of detectably labeled probes comprising a locus-specific probe for MYC, a locus-specific probe for FGFR1, a break-apart probe for ERG, and a locus-specific probe for MYCN, or (v) a set of detectably labeled probes comprising a locus-specific probe for MYC, a locus-specific probe for FGFR1, a break-apart probe for ERG, and a locus-specific probe for MDM2. Set (i) can further consist of, of the set of any of (ii)-(v) can further comprise, a chromosome enumeration probe for chromosome 8, a chromosome enumeration probe for chromosome 10, a locus-specific probe for AURKA, a locus-specific probe for NKX3.1, a locus-specific probe for P27, a break-apart probe for ETV1, and/or one or more probes for one or more genes involved in the same pathway as any of the foregoing genes. Use of a chromosome enumeration probe along with a locus-specific probe for a gene present on the same chromosome enables a ratio, such as the gene/chromosome ratio (e.g., PTEN/CEP10 and/or FGFR1/CEP8) to be assessed, if desired. The kit further comprises (b) instructions for identifying a patient with indolent, prostatic adenocarcinoma. The instructions comprise determining in a sample obtained from the patient the presence of chromosomal abnormalities. The method can comprise contacting the sample with a set of probes under hybridizing conditions, counting hybridization complexes, and comparing the number to a cut-off in a range of cut-offs or a specific cut-off as described herein. For example, for (i) a MYC % gain (% gain is % of cells with MYC copy numbers >2) of greater than or equal to two and/or a FGFR1% loss (% loss is % of cells with FGFR1 copy numbers <2) of greater than or equal to 10, for (ii) a MYC % gain (% gain is % of cells with MYC copy numbers >2) of greater than or equal to two, a FGFR1% loss (% loss is % of cells with FGFR1 copy numbers <2) of greater than or equal to 10, and/or an ERG % 2+Edel of greater than or equal to two, for (iii) a MYC % gain (% gain is % of cells with MYC copy numbers >2) of greater than or equal to two, a FGFR1% loss (% loss is % of cells with FGFR1 copy numbers <2) of greater than or equal to 10, an ERG % 2+Edel of greater than or equal to 10, and/or a PTEN % homozygous loss of greater than or equal to 20, for (iv) a MYC % gain (% gain is % of cells with MYC copy numbers >2) of greater than or equal to two, a FGFR1% loss (% loss is % of cells with FGFR1 copy numbers <2) of greater than or equal to 18, an ERG % 2+Edel of greater than or equal to two, and/or a MYCN % gain (% gain is % of cells with MYCN copy numbers >2) of greater than or equal to 20, or for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to two, and/or a MDM2% gain (% gain is % of cells with MDM2 copy numbers >2) of greater than or equal to three indicates that the patient has a high risk of developing aggressive, prostatic adenocarcinoma and none of the foregoing indicates that the patient has indolent, prostatic adenocarcinoma. The instructions can further comprise instructions for obtaining a clinical parameter selected from the group consisting of a Gleason score, a tumor stage, a level of prostate-specific antigen (PSA), a nomogram, methylation status, mutation, and age of the patient, any of which can be combined with the determination of the presence of chromosomal abnormalities for prognosis.

An above-described kit can further comprise one or more reagents, such as DAPI 1 counterstain, pre-treatment SSC buffer (e.g., 1×SSC, pH 7.0), protease buffer (e.g., 0.1 N HCl), protease IV (e.g., pepsin, such as in powder form (75 mg/tube)), post-hybridization wash buffer (e.g., 2×SSC, 0.3% NP-40), and the like.

EXAMPLES

The following examples serve to illustrate the present invention. The examples are not intended to limit the scope of the claimed invention in any way.

Example 1

This example describes the evaluation of various probes, and combinations thereof, in the assessment of prostate cancer samples using multicolor fluorescence in situ hybridization (FISH).

A total of 52 formalin-fixed, paraffin-embedded (FFPE) radical prostatectomy specimens from patients with adenocarcinoma of the prostate were collected at RUSH Medical Center, Chicago, Ill. Out of the 52 specimens, 32 were obtained from patients that progressed within 15 years. Out of those 32 specimens, seven were obtained from patients that were never disease-free, and four were obtained from patients that died from prostate carcinoma. The remaining 20 specimens were obtained from patients that did not progress during the period of follow-up from 8.2-15.0 years.

All specimens were evaluated with 14 probes. The probes were PTEN, NKX3.1, P27 (CDKN1B), CEP10, CMYC, AURKA, ERG Cen (centromeric probe), ERG Tel (telomeric probe), ETV1 Tel (telomeric probe), ETV1 Cen (centromeric probe), MDM2, MYCN, FGFR1, and CEP8. The probes were tested in sets as shown in Table 1. All probes were manufactured at Abbott Molecular, Inc. (Des Plaines, Ill.), and can be obtained from the manufacturer.

TABLE 1

| Probe Set | Probe | Locus | Color |
|---|---|---|---|
| Probe Set 1 | PTEN | 10q23 | Gold |
|  | CEP10 |  | Aqua |
|  | ERG Cen | 21q22.2 | Red |
|  | ERG Tel | 21q22.2 | Green |
| Probe Set 2 | NKX3.1 | 8p21 | Gold |
|  | CMYC | 8q24 | Aqua |
|  | ETV1 Tel | 7p21.2 | Red |
|  | ETV1 Cen | 7p21.2 | Green |
| Probe Set 3 | P27 (CDKN1B) | 12p13.1 | Gold |
|  | AURKA | 20q13.2 | Aqua |
|  | MDM2 | 12q14-15 | Red |
|  | MYCN | 2p24 | Green |
| Probe Set 4 | FGFR1 | 8p12 | Red |
|  | CEP8 |  | Aqua |

FFPE specimen slides were selected within 10 serial sections of the respective hematoxylin- and eosin-stained (H&E stained) slides for evaluation of the probes with FISH. This selection ensured minimal separation between the areas evaluated by histopathology and areas evaluated by FISH. The H&E stained sections were examined by a pathologist. The largest possible areas of tumors were marked, i.e., encircled. Corresponding areas on the specimen slides selected for evaluation of the probes with FISH were marked with a glass scribe.

FFPE specimen slides were baked at 60° C. for 2-24 hours and then treated three times with Hemo-De® (Scientific Safety Solvents, Keller, Tex.) for five minutes each time at room temperature and rinsed two times with 100% ethanol for one minute each time at room temperature. Slides were incubated in pre-treatment solution (1×SSC (saline-sodium citrate), pH 7.0) at 80° C. for 35 minutes, rinsed in deionized water for three minutes, incubated in 0.15% pepsin in 0.1 N HCl solution at 37° C. for 20-22 minutes, and rinsed again in deionized water for three minutes. Slides then were dehydrated in 70%, 85%, and 100% ethanol for one minute each and air-dried.

Ten microliters of a hybridization mixture containing a probe set (as indicated in Table 1), blocking DNAs, and LSI/WCP Hybridization Buffer (Abbott Molecular, Inc.) were added to a specimen slide, and a coverslip was applied and sealed with rubber cement. Slides and probes were co-denatured at 73° C. for five minutes and hybridized at 37° C. on a ThermoBrite® hybridization platform (Abbott Molecular, Inc.) for 16-24 hours. After hybridization, coverslips were removed by soaking the slides in 1×SSC solution, pH 7.0, for 2-5 minutes, and immediately washing in 2×SSC/0.3% NP-40 at 73° C. for three minutes and 1×SSC solution, pH 7.0, at room temperature for one minute. The slides then were allowed to dry in the dark. Ten microliters of 4',6-diamidino-2-phenylindole counterstain/anti-fade solution (DAPI 1; Abbott Molecular, Inc.) were added to the specimen, and the specimen was covered with a coverslip for microscopy.

Several fields of view within the scribed tumor area were evaluated on slides separately hybridized with each probe set listed in Table 1. Cells (50-100) were enumerated for the number of fluorescent signals for each probe in a given set. All possible patterns of rearrangement and copy number changes for the ERG and ETV1 break apart probes were captured and recorded.

The following FISH abnormality parameters were calculated:

ERG break-apart probe (BAP) (no. single red signals $\geq 1$),
ERG 2+Edel (no. single red signals—no. single green signals $\geq 2$),
PTEN loss (% cells per specimen with signal $\leq 1$),
PTEN/CEP10 loss (% cells per specimen with ratio <1),
ETV1 BAP (no. single red signals $\geq 1$),
NKX3.1 loss (% cells per specimen with signal $\leq 1$),
CMYC gain (% cells per specimen with signal >2),
AURKA gain (% cells per specimen with signal >2),
MYCN gain (% cells per specimen with signal >2),
P27 loss (% cells per specimen with signal $\leq 1$),
MDM2 gain (% cells per specimen with signal >2),
FGFR1 gain (% cells per specimen with signal >2),
FGFR1 loss (% cells per specimen with signal $\leq 1$),
CEP8 gain (% cells per specimen with signal >2),
CEP8 loss (% cells per specimen with signal $\leq 1$),
FGFR1/CEP8 gain (% cells per specimen with ratio >1), and
FGFR1/CEP8 loss (% cells per specimen with ratio <1).

The FISH abnormality parameters were systematically analyzed to select and prioritize candidate probes, and combinations thereof, using Receiver Operating Characteristic (ROC) analysis and Survival analysis (Cox Proportional Hazards model). Patients were followed up for 15 years. Patients, who developed progression beyond 15 years, were treated as censored at 15 years. Disease outcome was "progression," which included disease recurrence and death of disease (DOD) as outcomes. ROC analysis discriminated between those patients, who progressed within 15 years (sensitivity), and control patients, who did not progress within 15 years (specificity), in order to maximize sensitivity and specificity (Area Under the Curve (AUC)). Using Survival analysis, a Hazard Ratio (HR) of "the likelihood of disease progression in FISH-positive patients/FISH-negative patients" was determined. For each FISH abnormality parameter, highest specificity was optimized based on selected cutoff(s) to select patients for aggressive/adjuvant treatment (in this study, patients were selected for highest specificity to achieve the best "positive predictive value"). Highest sensitivity, with specificity of at least 50%, was optimized based on selected cutoff(s) to select patients with indolent tumors for observation (in this study, patients were selected for highest sensitivity to achieve the best "negative predictive value").

Using ROC analysis and Survival analysis, the abnormal FISH parameters in Table 2 were identified as having the potential to aid in discriminating patients with high risk for disease progression from those patients with low risk for disease progression with p<0.05. The cutoff was based on percentage of cells containing a genomic abnormality. FISH positivity and negativity were decided based on the cutoff values. FISH positivity was defined as the percentage of cells containing a genomic abnormality $\geq$cutoff, whereas FISH negativity was defined as the percentage of cells containing a genomic abnormality <cutoff. Each cutoff was determined by simulating all possible cutoffs (1-100%) from the Cox model, and only those cutoffs with significant p-values were included in the secondary ROC analysis to calculate the AUC. The cutoff value was selected by the best Hazard Ratio (HR). When HR was greater or equal to one, the largest HR was chosen; when HR was less than one, the smallest HR was chosen.

TABLE 2

| Abnormal FISH Parameter | Cutoff* | Hazard Ratio (best possible) | P-value (COX) | AUC |
| --- | --- | --- | --- | --- |
| FGFR1 loss | 40 | 4.163 | 0.0030 | 0.7039 |
| CEP8 loss | 26 | 3.858 | 0.0006 | 0.6977 |
| FGFR1 gain | 6 | 0.303 | 0.0122 | 0.6914 |
| FGFR1/CEP8 loss | 72 | 8.504 | 0.0475 | 0.6664 |
| CEP8 gain | 15 | 0.372 | 0.0136 | 0.6555 |
| CMYC gain | 26 | 2.695 | 0.0442 | 0.6422 |
| ERG single red | 17 | 0.264 | 0.0387 | 0.5648 |
| AURKA gain | 1 | 0.118 | 0.0475 | 0.5031 |

*the p-value was still significant within the cutoff ranges of 15-40 for FGFR1 loss, 21-36 for CEP8 % loss, 26-46 for FGFR1 gain, 13-72 for FGFR1/CEP8 loss, 15-40 for CEP8 gain, 2-30 for MYC gain, and 14-17 for ERG single red.

Example 2

This example describes further evaluation of FGFR1 gain with a cutoff of six and FGFR1 loss with a cutoff of 40.

FGFR1 gain with a cutoff of six was evaluated further as shown in FIG. 1. FIG. 1 is a KM curve (PFS (years) vs. survival probability) of FGFR1 gain with a log-rank p-value of 0.0062. The data indicated that patients with FGFR1 gain or amplification will progress (recur or die) slower. In other words, those patients, who are positive for FGFR1 gain, have less chance of progression than those patients, who are negative for FGFR1 gain (hazard ratio of 0.303).

Figure 2:
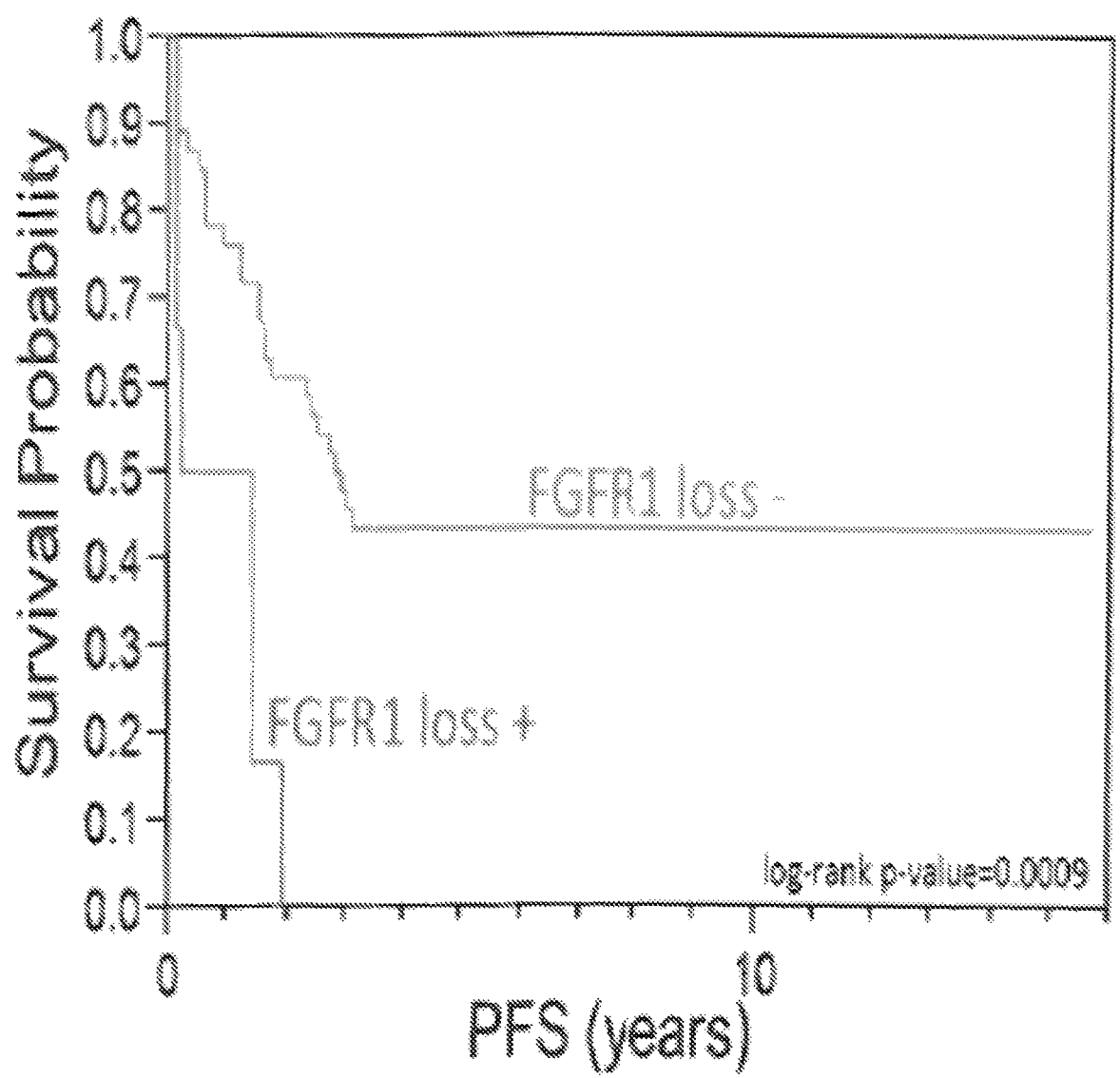
FIG. 2 is a KM curve (PFS (years) vs. survival probability) of FGFR1 loss with a cutoff of 40 and a log-rank p-value of 0.0009.

FGFR1 loss with a cutoff of 40 was evaluated further as shown in FIG. 2. FIG. 2 is a KM curve (PFS (years) vs. survival probability) of FGFR1 loss with a log-rank p-value of 0.0009. The data indicated that patients with FGFR1 loss will progress (recur or die) faster. In other words, those patients, who are positive for FGFR1 loss, have more chance of progression than those patients, who are negative for FGFR1 loss (hazard ratio of 4.163).

Example 3

This example describes further evaluation of combinations of two, three, and four abnormal FISH parameters.

Combinations of two, three, and four abnormal FISH parameters were evaluated using ROC analysis. AUC rankings of the combinations are shown in Table 3. Comparison of the analysis between combinations of abnormal FISH parameters and single abnormal FISH parameters by AUC indicated that maximum performance is achieved by grouping complementary biomarkers.

TABLE 3

| Combination | AUC |
|---|---|
| CMYC gain, ERG 2 + Edel, FGFR1 loss, PTEN homozygous loss | 0.8563 |
| CMYC gain, ERG 2 + Edel, FGFR1 loss, NKX3.1 loss | 0.8531 |
| CMYC gain, ERG 2 + Edel, FGFR1 loss, MYCN gain | 0.8445 |
| CMYC gain, ERG 2 + Edel, FGFR1 loss, MDM2 gain | 0.8438 |
| CMYC gain, ERG 2 + Edel, FGFR1 loss | 0.843 |
| CMYC gain, ETV1 single red, FGFR 1 gain, P27 loss | 0.8391 |
| CMYC gain, FGFR1 loss, PTEN homozygous loss, FGFR1/CEP8 loss | 0.8391 |
| CEP8 loss, CMYC gain, ERG 2 + Edel, FGFR1 gain | 0.8438 |
| CEP8 loss, CMYC gain, ERG 2 + Edel, NKX3.1 loss | 0.843 |
| CEP8 loss, CMYC gain, ERG 2 + Edel, FGFR1 loss | 0.8398 |
| CEP8 loss, CMYC gain, ERG 2 + Edel, MYCN gain | 0.8398 |
| CEP8 loss, CMYC gain, ERG 2 + Edel, MDM2 gain | 0.8359 |
| CEP8 loss, CMYC gain, ETV1 single red, FGFR1 gain | 0.8375 |
| CEP8 loss, CMYC gain, ERG 2 + Edel, FGFR1/CEP8 loss | 0.8438 |
| CEP8 loss, CMYC gain, ETV1 single red, FGFR1 loss | 0.8359 |
| AURKA gain, CMYC gain, ERG 2 + Edel, FGFR1 loss | 0.8383 |
| CEP8 loss, CMYC gain, ERG 2 + Edel, PTEN loss | 0.8359 |
| CMYC gain, ERG 2 + Edel, FGFR1 loss, P27 loss | 0.8359 |
| AURKA gain, CEP8 loss, CMYC gain, ERG 2 + Edel | 0.8336 |
| CMYC gain, FGFR1 loss | 0.8055 |

Example 4

This example describes the further evaluation of combinations of abnormal FISH parameters in the selection of patients with more aggressive disease for aggressive and/or adjuvant treatment.

Various combinations of abnormal FISH parameters were evaluated using COX and ROC analysis for selection of patients with more aggressive disease for aggressive and/or adjuvant treatment. Combinations of abnormal FISH parameters with the highest specificity and acceptable sensitivity were selected so as to target the highest positive predictive value. The results of COX and ROC analysis of six combinations are set forth in Table 4. Each cutoff was determined by first simulating all possible cutoff combinations (for each parameter in the combination). The cutoff was based on the percentage of cells containing a genomic abnormality. FISH positivity and negativity were decided based on the cutoff values. FISH positivity was defined as any parameters in the combination being positive, whereas FISH negativity was defined as all FISH parameters in the combination being negative. The Cox model was applied to each cutoff combination. Only those cutoff combinations with significant p-values were included in a secondary ROC analysis. Then the cutoff value was determined from ROC.

TABLE 4

| Combination of Abnormal FISH Parameters | Cutoff 1 | Cutoff 2 | Cutoff 3 | Cutoff 4 | Sensitivity | Specificity | Hazard Ratio | P-value (Cox) | AUC |
|---|---|---|---|---|---|---|---|---|---|
| CMYC gain, FGFR1 loss | 26 | 26 | NA | NA | 44% | 100% | 3.874 | 0.0003 | 0.8055 |
| CMYC gain, ERG 2 + Edel, FGFR1 loss | 14 | 10 | 26 | NA | 53% | 95% | 3.915 | 0.0002 | 0.8430 |
| CMYC gain, ERG 2 + Edel, FGFR1 loss, PTEN homozygous loss | 8 | 10 | 26 | 20 | 59% | 80% | 2.807 | 0.0047 | 0.8563 |
| CMYC gain, ERG 2 + Edel, FGFR1 loss, MYCN gain | 30 | 10 | 20 | 20 | 81% | 75% | 5.328 | 0.0003 | 0.8445 |
| CMYC gain, ERG 2 + Edel, FGFR1 loss, MDM2 gain | 30 | 10 | 20 | 10 | 78% | 65% | 3.447 | 0.0041 | 0.8438 |
| CMYC gain, FGFR1 loss, PTEN homozygous loss, FGFR1/CEP8 loss | 26 | 26 | 20 | 34 | 50% | 85% | 2.360 | 0.0166 | 0.8391 |

Figure 3:
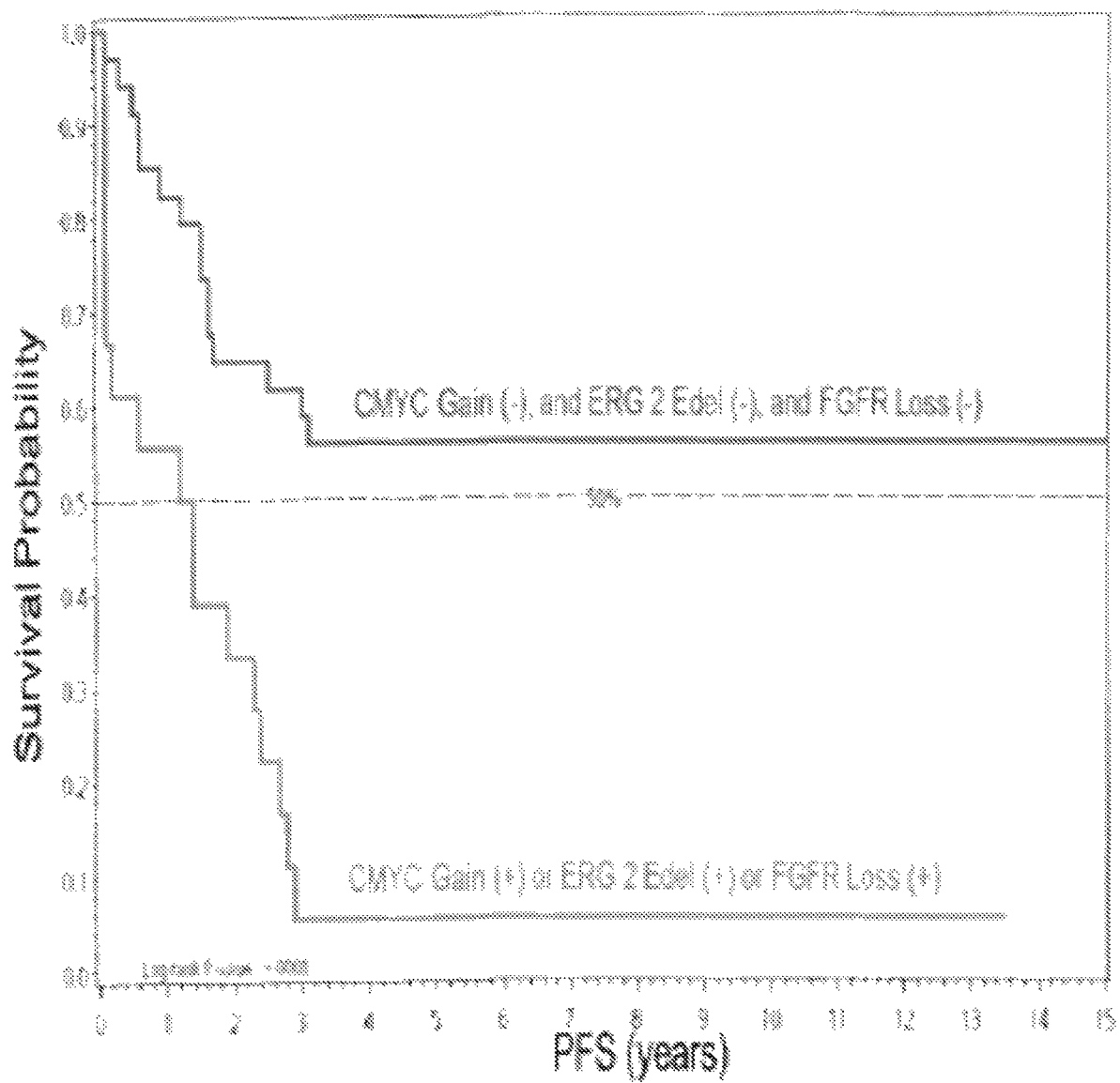
FIG. 3 is a KM curve (PFS (years) vs. survival probability) of CMYC gain, ERG 2+Edel, and FGFR1 loss with a log-rank p-value of 0.0001.

The combination of CMYC gain, ERG 2+Edel, and FGFR1 loss was evaluated further as shown in FIG. 3. FIG. 3 is a KM curve (PFS (years) vs. survival probability) of CMYC gain, ERG 2+Edel, and FGFR1 loss with a log-rank p-value of 0.0001.

The data for the analysis of prognosis by high/low risk (i.e., FISH-positive/FISH-negative) are shown in Table 5. With a high specificity (95.00%), an acceptable sensitivity (53.13%), and a hazards radio of 3.92, the combination of CMYC gain, ERG 2+Edel, and FGFR1 loss indicated that patients, who are FISH-positive, have a greater chance of progression and will progress more quickly than patients, who are FISH-negative. This combination of abnormal FISH parameters could separate a high risk (recurred or DOD) group from a low risk (indolent) group and could help patients and clinicians to decide to seek immediate treatment.

Various combinations of abnormal FISH parameters were evaluated using COX and ROC analysis for selection of patients with less aggressive (indolent) tumors for observation. Combinations of abnormal FISH parameters with the highest sensitivity and at least 50% specificity were selected so as to target the highest negative predictive value. The results of COX and ROC analysis of six combinations are set forth in Table 6. Each cutoff was determined by first simulating all possible cutoff combinations (for each parameter in the combination). The cutoff was based on the percentage of cells containing a genomic abnormality. FISH positivity and negativity was decided based on the cutoff values. FISH positivity was defined as any parameters in the combination being positive, whereas FISH negativity was defined as all FISH parameters in the combination being negative. The Cox model was applied to each cutoff combination. Only those cutoff combinations with significant p-value were included in a secondary ROC analysis. Then the cutoff value was determined from ROC.

TABLE 5

| Combination of Abnormal FISH Parameters | High/Low Risk | N (number progressed/DOD) | Median Survival (95% CI) | Hazard Ratio (95% CI) | P-value (Cox) | Sensitivity | Specificity |
| --- | --- | --- | --- | --- | --- | --- | --- |
| CMYC gain, ERG 2 + Edel, FGFR1 loss | High Risk | 18(17) | 1 (0.1, 2.3) | 3.92 (1.9, 8.05) | 0.0002 | 53.13% | 95.00% |
| | Low Risk | 34(15) | NA (1.6, NA) | | | | |

Example 5

This example describes the further evaluation of combinations of abnormal FISH parameters in the identification of patients with less aggressive (indolent) tumors for observation.

TABLE 6

| Combination of Abnormal FISH Parameters | Cutoff 1 | Cutoff 2 | Cutoff 3 | Cutoff 4 | Sensitivity | Specificity | Hazard Ratio | P-value (Cox) | AUC |
| --- | --- | --- | --- | --- | --- | --- | --- | --- | --- |
| CMYC gain, FGFR1 loss | 2 | 10 | NA | NA | 88% | 50% | 3.571 | 0.0177 | 0.8055 |
| CMYC gain, ERG 2 + Edel, FGFR1 loss | 2 | 2 | 10 | NA | 91% | 50% | 4.648 | 0.0116 | 0.8430 |
| CMYC gain, ERG 2 + Edel, FGFR1 loss, PTEN homozygous loss | 2 | 10 | 10 | 20 | 91% | 50% | 4.648 | 0.0116 | 0.8563 |
| CMYC gain, ERG 2 + Edel, FGFR1 loss, MYCN gain | 2 | 2 | 18 | 20 | 97% | 50% | 14.200 | 0.0092 | 0.8445 |
| CMYC gain, ERG 2 + Edel, FGFR1 loss, MDM2 gain | 30 | 2 | 20 | 3 | 94% | 55% | 8.665 | 0.0032 | 0.8438 |
| CMYC gain, FGFR1 loss, PTEN homozygous loss, FGFR/CEP8 loss | 2 | 10 | 20 | 35 | 91% | 50% | 4.648 | 0.0116 | 0.8391 |

Figure 4:
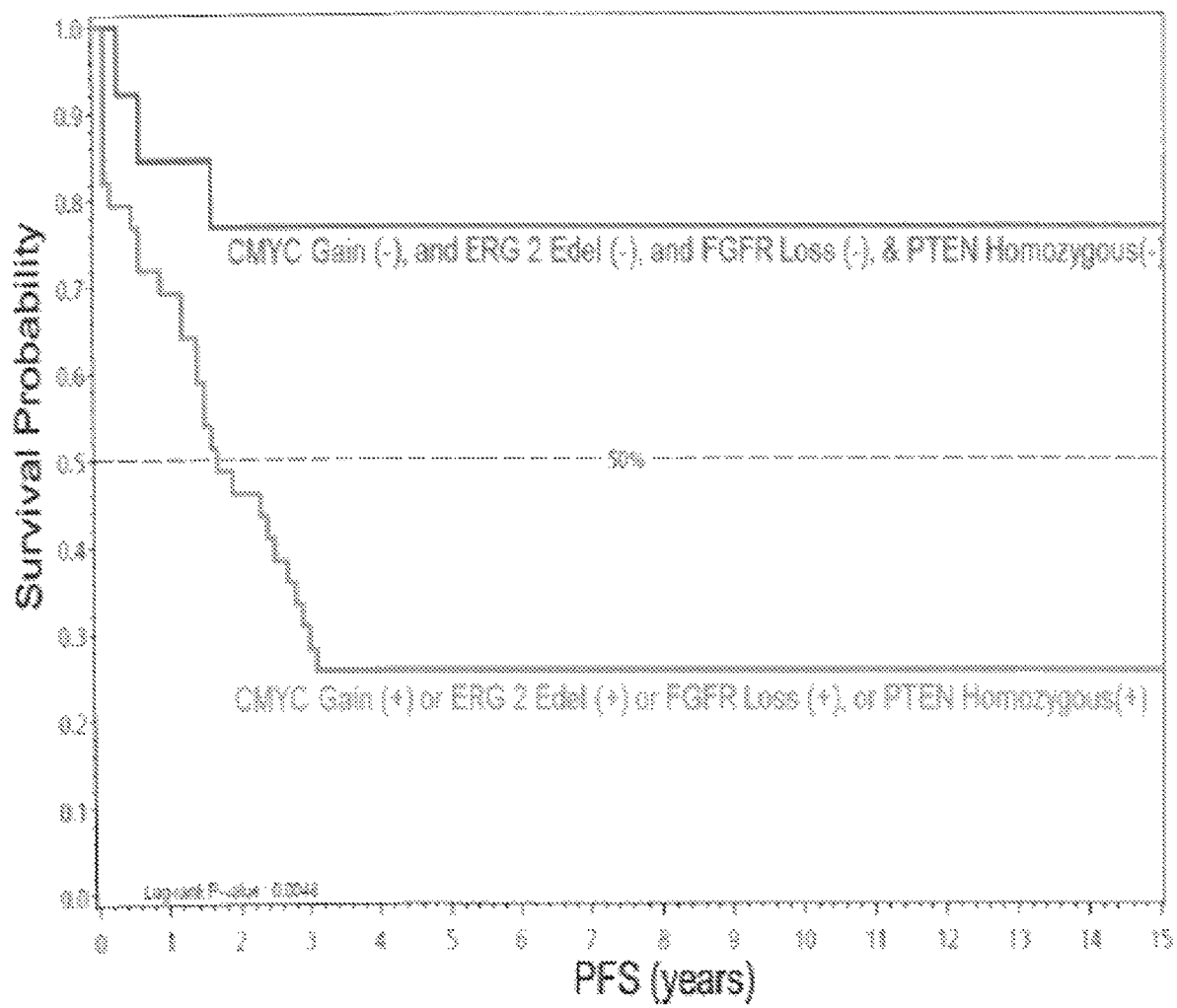
FIG. 4 is a KM curve (PFS (years) vs. survival probability) of CMYC gain, ERG 2+Edel, FGFR1 loss, and homozygous loss for PTEN with a log-rank p-value of 0.0048.

The combination of CMYC gain, ERG 2+Edel, FGFR1 loss, and homozygosity for PTEN was evaluated further as shown in FIG. 4. FIG. 4 is a KM curve (PFS (years) vs. survival probability) of CMYC gain, ERG 2+Edel, FGFR1 loss, and homozygosity for PTEN with a log-rank p-value of 0.0048.

The data for the analysis of prognosis by high/low risk (i.e., FISH-positive/FISH-negative) are shown in Table 7. With a high sensitivity (90.60%), an acceptable sensitivity (50.00%), and a hazards radio of 4.65, the combination of CMYC gain, ERG 2+Edel, FGFR1 loss, and homozygous loss for PTEN indicated that patients, who are FISH-positive, have a greater chance of progression and will progress more quickly than patients, who are FISH-negative. More importantly, this combination of abnormal FISH parameters also has the potential to predict that those patients, who are FISH-negative (10/13 patients were progression-free within 15 follow-up years shown on the KM curve (top line) in FIG. 4), are expected to have a longer progression-free time. This probe combination could separate the low risk (indolent) from the high risk (recurred or DOD) group and could help patients and clinicians decide to choose active surveillance (AS) with peace of mind if FISH data are negative.

TABLE 7

| Combination of Abnormal FISH Parameters | High/Low Risk | N (number progressed/DOD) | Median Survival (95% CI) | Hazard Ratio (95% CI) | P-value (Cox) | Sensitivity | Specificity |
|---|---|---|---|---|---|---|---|
| CMYC gain, ERG 2 + Edel, FGFR1 loss, PTEN homozygous loss | High Risk | 39(29) | 2 (1.2, 2.8) | 4.65 (1.41, 15.33) | 0.0116 | 90.63% | 50.00% |
|  | Low Risk | 13(3) | NA (1.6, NA) |  |  |  |  |

Example 6

This example describes how adding other clinical parameters, such as Gleason score, to analysis of a combination of abnormal FISH parameters can improve prediction of disease progression.

Figure 5A:
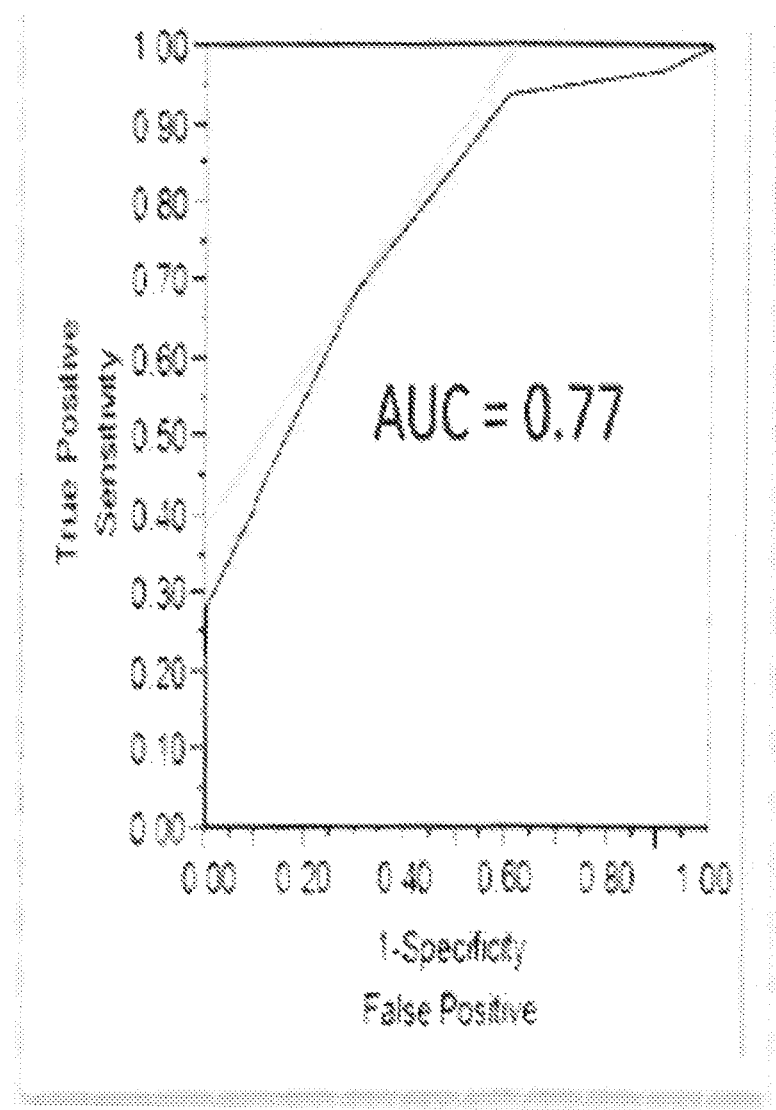
FIG. 5A is a ROC curve, which is a graph of 1-Specificity (false positive) vs. Sensitivity (true positive), which shows the AUC with Gleason score alone.
Figure 5B:
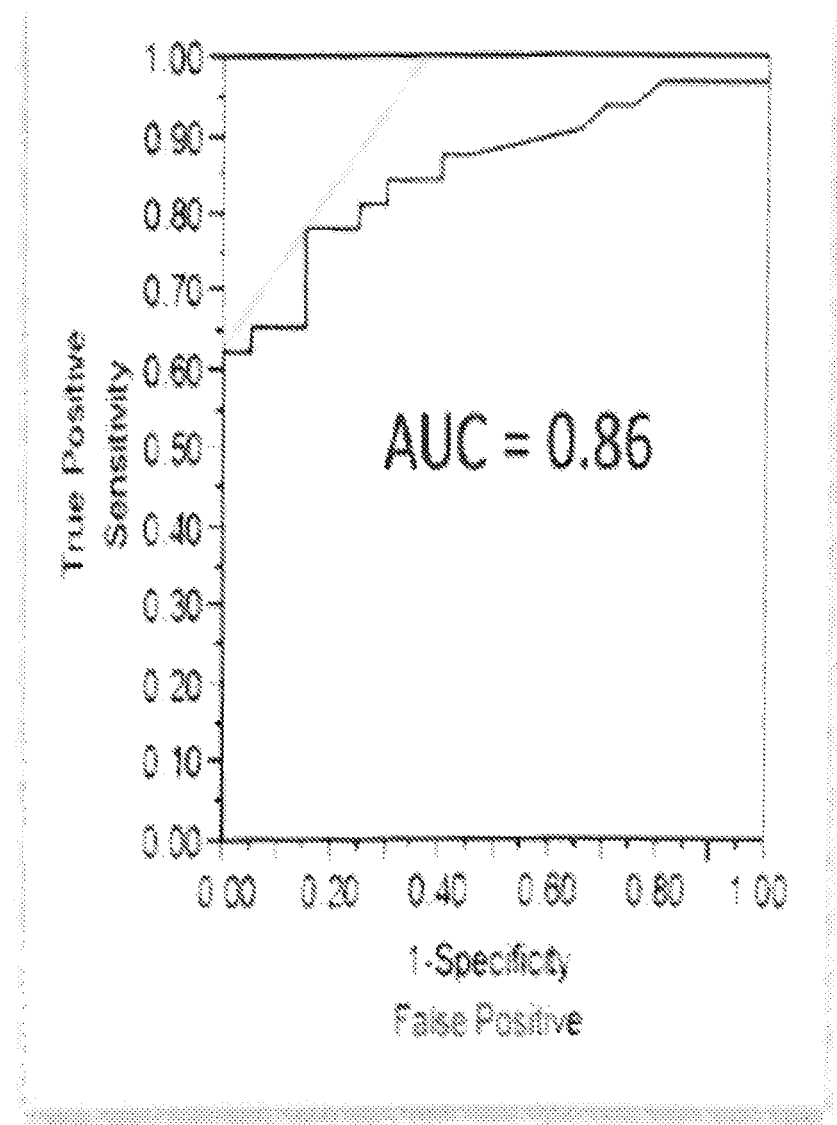
FIG. 5B is a ROC curve, which is a graph of 1-Specificity (false positive) vs. Sensitivity (true positive), which shows the AUC with the combination of abnormal FISH parameters CMYC gain, ERG 2+Edel, FGFR1 loss, and PTEN homozygous loss.
Figure 5C:
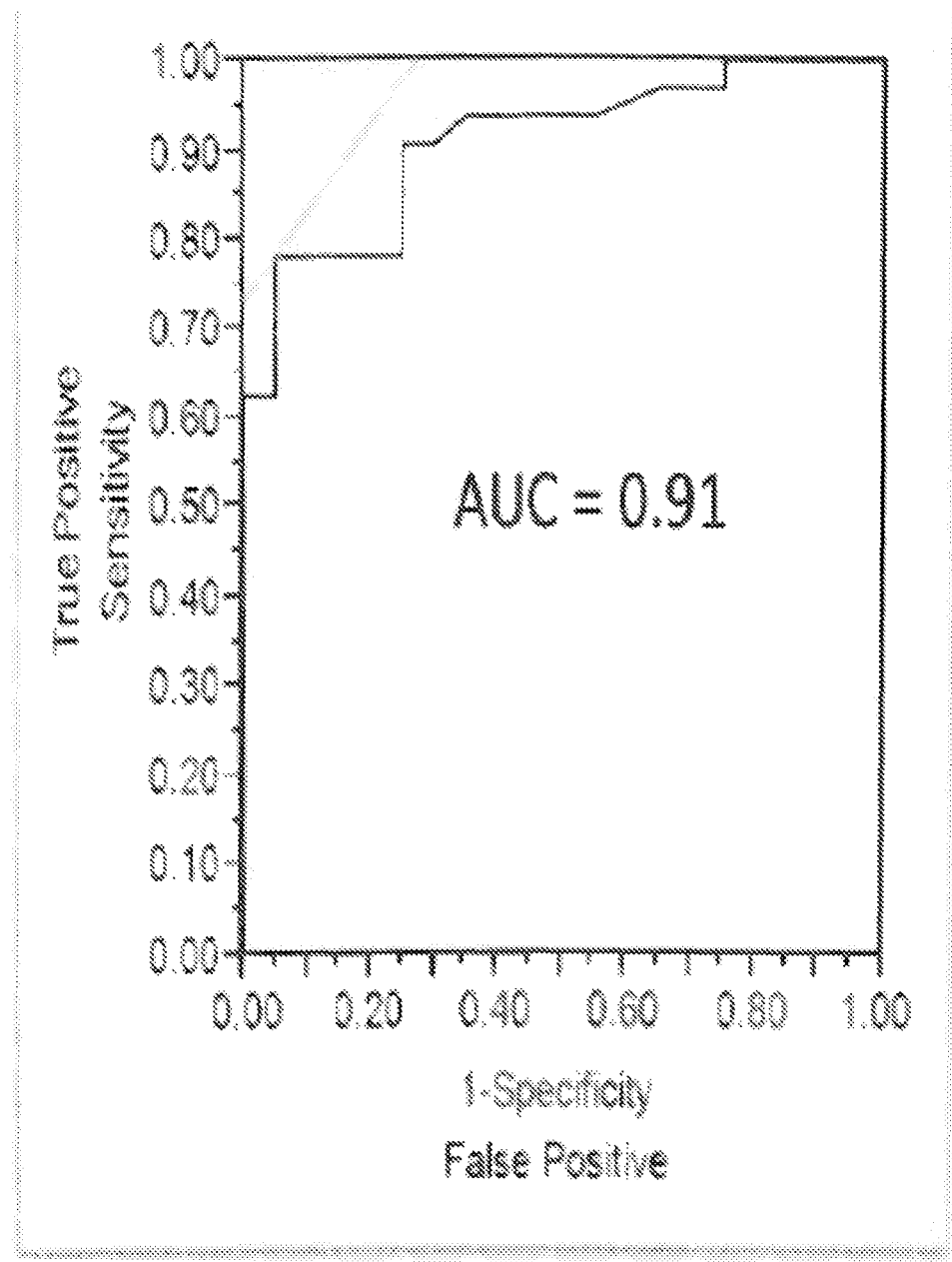
FIG. 5C is a ROC curve, which is a graph of 1-Specificity (false positive) vs. Sensitivity (true positive), which shows the AUC with the Gleason score and the combination of abnormal FISH parameters CMYC gain, ERG 2+Edel, FGFR1 loss, and PTEN homozygous.

Analysis of a combination of abnormal FISH parameters, such as one of the combinations set forth in Table 3, or more specifically in Table 4 or Table 6, can be combined with one or more other clinical parameters, such as Gleason score, tumor stage, prostate-specific antigen (PSA), patient age, and the like, to predict disease progression. As shown in FIGS. 5A-5C, which are ROC curves, which are graphs of 1-Specificity (false positive) vs. Sensitivity (true positive), certain combinations of four abnormal FISH parameters provided incremental value to a Gleason score. FIG. 5A shows the AUC with Gleason score alone, whereas FIG. 5B shows the AUC with the combination of abnormal FISH parameters CMYC gain, ERG 2+Edel, FGFR1 loss, and PTEN homozygous loss, and FIG. 5C shows the AUC with the Gleason score and the combination of abnormal FISH parameters CMYC gain, ERG 2+Edel, FGFR1 loss, and PTEN homozygous loss.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of" and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

For reasons of completeness, various aspects of the invention are set out in the following numbered clauses:

Clause 1. A method of distinguishing between a patient with aggressive, prostatic adenocarcinoma and a patient with indolent, prostatic adenocarcinoma, which method comprises:
  (a) contacting a sample from the patient with:
    (i) a set of detectably labeled probes consisting of a locus-specific probe for MYC and a locus-specific probe for FGFR1,
    (ii) a set of detectably labeled probes comprising a locus-specific probe for MYC, a locus-specific probe for FGFR1, and a break-apart probe for ERG,
    (iii) a set of detectably labeled probes comprising a locus-specific probe MYC, a locus-specific probe for FGFR1, a break-apart probe for ERG, and a locus-specific probe for PTEN, (iv) a set of detectably labeled probes comprising a locus-specific probe for MYC, a locus-specific probe for FGFR1, a break-apart probe for ERG, and a locus-specific probe for MYCN, (v) a set of detectably labeled probes comprising a locus-specific probe for MYC, a locus-specific probe for FGFR1, a break-apart probe for ERG, and a locus-specific probe for MDM2, (vi) a set of detectably labeled probes comprising a locus-specific probe for MYC, a locus-specific probe for FGFR1, a break-apart probe for ERG, and a locus-specific probe for NKX3.1, (vii) a set of detectably labeled probes comprising a locus-specific probe for MYC, a break-apart probe for ETV1, a locus-specific probe for FGFR1, and a locus-specific probe for P27, (viii) a set of detectably labeled probes comprising a locus-specific probe for MYC, a locus-specific probe for FGFR1, a locus-specific probe for PTEN, and a chromosome enumeration probe for chromosome 8 (CEP8), (ix) a set of detectably labeled probes comprising a chromosome enumeration probe for chromosome 8, a locus-specific probe for MYC, a break-part probe for ERG, and a locus-specific probe for FGFR1, (x) a set of detectably labeled probes comprising a chromosome enumeration probe for chromosome 8, a locus-specific probe for MYC, a break-apart probe for ERG, and a locus-specific probe for NKX3.1, (xi) a set of detectably labeled probes comprising a chromosome enumeration probe for chromosome 8, a locus-specific probe for MYC, a break-apart probe for ERG, and a locus-specific probe for FGFR1, (xii) a set of detectably labeled probes comprising a chromosome enumeration probe for chromosome 8, a locus-specific probe for MYC, a break-apart probe for ERG, and a locus-specific probe for MYCN, (xiii) a set of detectably labeled probes comprising a chromosome enumeration probe for chromosome 8, a locus-specific probe for MYC, a break-apart probe for ERG, and a locus-specific probe for MDM2, (xiv) a set of detectably labeled probes comprising a chromosome enumeration probe for chromosome 8, a locus-specific probe for MYC, a break-apart probe for ETV1, and a locus-specific probe for FGFR1, (xv) a set of detectably labeled probes comprising a locus-specific probe for AURKA, a locus-specific probe for MYC, a break-apart probe for ERG, and a locus-specific probe for FGFR1, (xvi) a set of detectably labeled probes comprising a chromosome enumeration probe for chromosome 8, a locus-specific probe for MYC, a break-apart probe for ERG, and a locus-specific probe for PTEN, (xvii) a set of detectably labeled probes comprising a locus-specific probe for MYC, a break-apart probe for ERG, a locus-specific probe for FGFR1, and a locus-specific probe for P27, or (xviii) a set of detectably labeled probes comprising a locus-specific probe for AURKA, a chromosome enumeration probe for chromosome 8, a locus-specific probe for MYC, and a break-apart probe for ERG, under hybridizing conditions, wherein the locus-specific probe for FGFR1 in the sets of (i)-(vi), (viii), (xi), (xiv), (xv), and (xvii) is used to determine % loss of FGFR1, wherein the locus-specific probe for FGFR1 in the sets of (vii), (ix), and, as an alternative to % loss of FGFR1, (xiv), is used to determine % gain of FGFR1, wherein CEP8 in the sets of (ix)-(xiv), (xvi), and (xviii) is used to determine % loss of CEP8, wherein the locus-specific probe for PTEN in sets (iii) and (viii) is used to determine % homozygous loss of PTEN, wherein the locus-specific probe for PTEN in set (xvi) is used to determine % loss of PTEN, and wherein the locus-specific probe for FGFR1 and CEP8 in the sets of (viii), and as an alternative to % gain of FGFR1, (ix), are used to determine % loss of FGFR1/CEP8 ratio, and (b) determining the presence of a chromosomal abnormality in the sample, wherein a MYC % gain (% gain is % of cells with MYC copy numbers >2) of greater than or equal to two to less than or equal to 30, wherein a FGFR1% loss (% loss is % of cells with FGFR copy numbers <2) of greater than or equal to 15 to less than or equal to 40, wherein a FGFR1% gain (% gain is % of cells with FGFR copy numbers >2) of greater than or equal to two to less than or equal to 46, wherein a CEP8% loss (% loss is % of cells with CEP8 copy numbers <2) of greater than or equal to 21 to less than or equal to 36, wherein a CEP8% gain (% gain is % of cells with CEP8 copy numbers >2) of greater than or equal to 15 to less than or equal to 40, wherein a FGFR1/CEP8% loss of greater than or equal to 13 to less than or equal to 72, wherein a PTEN % homozygous loss (% homozygous loss is % of cells with PTEN copy numbers of zero) of greater than or equal to two and less than or equal to 40, wherein a PTEN % loss (% loss is % of cells with PTEN copy number of less than two) of greater than or equal to 10 to less than or equal to 50, wherein a ERG 2+Edel of greater than or equal to one to less than or equal to 30, wherein a MYCN % gain (% gain is % of cells with MYCN copy numbers >2) of greater than or equal to two to less than or equal to 30, wherein a MDM2% gain (% gain is % of cells with MDM2 copy numbers >2) of greater than or equal to two to less than or equal to 20, wherein a NKX3.1% loss (% loss is % of cells with NKX3.1 copy numbers <2) of greater than or equal to 10 to less than or equal to 50, wherein an ETV1% translocation/deletion of greater than or equal to 1 to less than or equal to 20, wherein a P27% loss (% loss is % of cells with P27 copy numbers <2) of greater than or equal to 10 to less than or equal to 50, or wherein an AURKA % gain (% gain is % of cells with AURKA copy numbers >2) of greater than or equal to 1 to less than or equal to 20 indicates that the patient has a high risk of developing aggressive, prostatic adenocarcinoma, whereas none of the above indicates that the patient has indolent, prostatic adenocarcinoma, whereupon a patient with aggressive, prostatic adenocarcinoma is distinguished from a patient with indolent, prostatic adenocarcinoma.

Clause 2. The method of clause 1, wherein, if a patient has had a prostatectomy, the determination of the presence of a chromosomal abnormality in the sample indicates that the patient has a high risk of recurrence or metastasis.

Clause 3. The method of clause 2, which further comprises recommending that the patient consult his physician for immediate treatment to inhibit or prevent recurrence or metastasis.

Clause 4. The method of clause 1, wherein, if a patient has/is being initially diagnosed with prostate cancer and the patient has a high risk of developing aggressive, prostatic adenocarcinoma, the method further comprises recommending that the patient consult his physician for immediate treatment.

Clause 5. The method of clause 1, wherein, if a patient has/is being initially diagnosed with prostate cancer and the patient has indolent, prostatic adenocarcinoma, the method further comprises recommending active surveillance or watchful waiting.

Clause 6. A method of identifying a patient with a high risk of developing aggressive, prostatic adenocarcinoma, which method comprises:
(a) contacting a sample from the patient with:
  (i) a set of detectably labeled probes consisting of a locus-specific probe for MYC and a locus-specific probe for FGFR1,
  (ii) a set of detectably labeled probes comprising a locus-specific probe for MYC, a locus-specific probe for FGFR1, and a break-apart probe for ERG,
  (iii) a set of detectably labeled probes comprising a locus-specific probe MYC, a locus-specific probe for FGFR1, a break-apart probe for ERG, and a locus-specific probe for PTEN,
  (iv) a set of detectably labeled probes comprising a locus-specific probe for MYC, a locus-specific probe for FGFR1, a break-apart probe for ERG, and a locus-specific probe for MYCN, or
  (v) a set of detectably labeled probes comprising a locus-specific probe for MYC, a locus-specific probe for FGFR1, a break-apart probe for ERG, and a locus-specific probe for MDM2, under hybridizing conditions, and
(b) determining the presence of chromosomal abnormalities in the sample,
  wherein for (i) a MYC % gain (% gain is % of cells with MYC copy numbers >2) of greater than or equal to 26 and/or a FGFR1% loss (% loss is % of cells with FGFR1 copy numbers <2) of greater than or equal to 26,
  wherein for (ii) a MYC % gain (% gain is % of cells with MYC copy numbers >2) of greater than or equal to 14, a FGFR1% loss (% loss is % of cells with FGFR1 copy numbers <2) of greater than or equal to 26, and/or an ERG % 2+Edel of greater than or equal to 10,
  wherein for (iii) a MYC % gain (% gain is % of cells with MYC copy numbers >2) of greater than or equal to eight, a FGFR1% loss (% loss is % of cells with FGFR1 copy numbers <2) of greater than or equal to 26, an ERG % 2+Edel of greater than or equal to 10, and/or a PTEN % homozygous loss of greater than or equal to 20,
  wherein for (iv) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MYCN % gain (% gain is % of cells with MYCN copy numbers >2) of greater than or equal to 20, or
  wherein for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to 10, and/or a MDM2% gain (% gain is % of cells with MDM2 copy numbers >2) of greater than or equal to 10 indicates that the patient has a high risk of developing aggressive, prostate adenocarcinoma, whereupon a patient with a high risk of developing aggressive, prostatic adenocarcinoma is identified.

Clause 7. The method of clause 6, wherein (i) further consists of, or any of (ii)-(v) further comprises, a chromosome enumeration probe for chromosome 8, a chromosome enumeration probe for chromosome 10, a locus-specific probe for AURKA, a locus-specific probe for NKX3.1, a locus-specific probe for P27, and/or a break-apart probe for ETV1.

Clause 8. The method of clause 6 or 7, which further comprises obtaining a clinical parameter selected from the group consisting of a Gleason score, a tumor stage, a level of prostate-specific antigen (PSA), a nomogram, methylation status, mutation, and age of the patient, any of which can be combined with the determination of the presence of chromosomal abnormalities for prognosis.

Clause 9. The method of any of clauses 6-8, which comprises:
(a) contacting a sample from the patient with a set of detectably labeled probes comprising a locus-specific probe for MYC, a locus-specific probe for FGFR1, and a break-apart probe for ERG under hybridizing conditions, and
(b) determining the presence of chromosomal abnormalities in the sample,
  wherein one or more of a MYC % gain (% gain is % of cells with MYC copy numbers >2) of greater than or equal to 14, an FGFR1% loss (% loss is % of cells with FGFR1 copy numbers <2) of greater than or equal to 26, and a ERG % 2+Edel of greater than or equal to 10 indicates that the patient has a high risk of developing aggressive, prostatic adenocarcinoma.

Clause 10. A method of identifying a patient with indolent, prostatic adenocarcinoma, which method comprises:
(a) contacting a sample from the patient with:
  (i) a set of detectably labeled probes consisting of a locus-specific probe for MYC and a locus-specific probe for FGFR1,
  (ii) a set of detectably labeled probes comprising a locus-specific probe for MYC, a locus-specific probe for FGFR1, and a break-apart probe for ERG,
  (iii) a set of detectably labeled probes comprising a locus-specific probe MYC, a locus-specific probe for FGFR1, a break-apart probe for ERG, and a locus-specific probe for PTEN,
  (iv) a set of detectably labeled probes comprising a locus-specific probe for MYC, a locus-specific probe for FGFR1, a break-apart probe for ERG, and a locus-specific probe for MYCN, or
  (v) a set of detectably labeled probes comprising a locus-specific probe for MYC, a locus-specific probe for FGFR1, a break-apart probe for ERG, and a locus-specific probe for MDM2, under hybridizing conditions, and
(b) determining the presence of chromosomal abnormalities in the sample,
  wherein for (i) a MYC % gain (% gain is % of cells with MYC copy numbers >2) of greater than or equal to two and/or a FGFR1% loss (% loss is % of cells with FGFR1 copy numbers <2) of greater than or equal to 10, wherein for (ii) a MYC % gain (% gain is % of cells with MYC copy numbers >2) of greater than or equal to two, a FGFR1% loss (% loss is % of cells with FGFR1 copy numbers <2) of greater than or equal to 10, and/or an ERG % 2+Edel of greater than or equal to two, wherein for (iii) a MYC % gain (% gain is % of cells with MYC copy numbers >2) of greater than or equal to two, a FGFR1% loss (% loss is % of cells with FGFR1 copy numbers <2) of greater than or equal to 10, an ERG % 2+Edel of greater than or equal to 10, and/or a PTEN % homozygous loss of greater than or equal to 20, wherein for (iv) a MYC % gain (% gain is % of cells with MYC copy numbers >2) of greater than or equal to two, a FGFR1% loss (% loss is % of cells with FGFR1 copy numbers <2) of greater than or equal to 18, an ERG % 2+Edel of greater than or equal to two, and/or a MYCN % gain (% gain is % of cells with MYCN copy numbers >2) of greater than or equal to 20, or wherein for (v) a MYC % gain (% gain is % of cells with MYC copy numbers >2) of greater than or equal to 30, a FGFR1% loss (% loss is % of cells with FGFR1 copy numbers <2) of greater than or equal to 20, an ERG % 2+Edel of greater than or equal to two, and/or a MDM2% gain (% gain is % of cells with MDM2 copy numbers >2) of greater than or equal to three, indicates that the patient has a high risk of developing aggressive, prostatic adenocarcinoma and none of the foregoing indicates that the patient has indolent, prostatic adenocarcinoma, whereupon a patient with indolent, prostatic adenocarcinoma is identified.

Clause 11. The method of clause 10, wherein (i) further consists of, or any of (ii)-(v) further comprises, a chromosome enumeration probe for chromosome 8, a chromosome enumeration probe for chromosome 10, a locus-specific probe for AURKA, a locus-specific probe for NKX3.1, a locus-specific probe for P27, and/or a break-apart probe for ETV1.

Clause 12. The method of clause 10 or 11, which further comprises obtaining a clinical parameter selected from the group consisting of a Gleason score, a tumor stage, a level of PSA, a nomogram, methylation status, mutation, and age of the patient, any of which can be combined with the determination of the presence of chromosomal abnormalities for prognosis.

Clause 13. The method of any of clauses 10-12, which comprises:
(a) contacting a sample from the patient with a set of detectably labeled probes comprising a locus-specific probe for MYC, a locus-specific probe for FGFR1, a locus-specific probe for PTEN, and a break-apart probe for ERG under hybridizing conditions, and
(b) determining the presence of chromosomal abnormalities in the sample,
wherein one or more of a MYC % gain (% gain is % of cells with MYC copy numbers >2) of greater than or equal to two, an FGFR1% loss (% loss is % of cells with FGFR1 copy numbers <2) of greater than or equal to 10, a PTEN % homozygous loss of greater than or equal to 20, and a ERG % 2+Edel of greater than or equal to 10 indicates that the patient has a high risk of developing aggressive, prostatic adenocarcinoma and none of the foregoing indicates that the patient has indolent, prostatic adenocarcinoma.

Clause 14. A set of detectably labeled probes, wherein the set of probes is:
(i) a set of detectably labeled probes consisting of a locus-specific probe for MYC and a locus-specific probe for FGFR1,
(ii) a set of detectably labeled probes comprising a locus-specific probe for MYC, a locus-specific probe for FGFR1, a break-apart probe for ERG, and a locus-specific probe for NKX3.1,
(iii) a set of detectably labeled probes comprising a locus-specific probe for MYC, a break-apart probe for ETV1, a locus-specific probe for FGFR1, and a locus-specific probe for P27,
(iv) a set of detectably labeled probes comprising a locus-specific probe for MYC, a locus-specific probe for FGFR1, a locus-specific probe for PTEN, and a chromosome enumeration probe for chromosome 8,
(v) a set of detectably labeled probes comprising a chromosome enumeration probe for chromosome 8, a locus-specific probe for MYC, a break-part probe for ERG, and a locus-specific probe for FGFR1,
(vi) a set of detectably labeled probes comprising a chromosome enumeration probe for chromosome 8, a locus-specific probe for MYC, a break-apart probe for ERG, and a locus-specific probe for NKX3.1,
(vii) a set of detectably labeled probes comprising a chromosome enumeration probe for chromosome 8, a locus-specific probe for MYC, a break-apart probe for ERG, and a locus-specific probe for FGFR1,
(viii) a set of detectably labeled probes comprising a chromosome enumeration probe for chromosome 8, a locus-specific probe for MYC, a break-apart probe for ERG, and a locus-specific probe for MYCN,
(ix) a set of detectably labeled probes comprising a chromosome enumeration probe for chromosome 8, a locus-specific probe for MYC, a break-apart probe for ERG, and a locus-specific probe for MDM2,
(x) a set of detectably labeled probes comprising a chromosome enumeration probe for chromosome 8, a locus-specific probe for MYC, a break-apart probe for ETV1, and a locus-specific probe for FGFR1,
(xi) a set of detectably labeled probes comprising a locus-specific probe for AURKA, a locus-specific probe for MYC, a break-apart probe for ERG, and a locus-specific probe for FGFR1,
(xii) a set of detectably labeled probes comprising a chromosome enumeration probe for chromosome 8, a locus-specific probe for MYC, a break-apart probe for ERG, and a locus-specific probe for PTEN,
(xiii) a set of detectably labeled probes comprising a locus-specific probe for MYC, a break-apart probe for ERG, a locus-specific probe for FGFR1, and a locus-specific probe for P27, or
(xiv) a set of detectably labeled probes comprising a locus-specific probe for AURKA, a chromosome enumeration probe for chromosome 8, a locus-specific probe for MYC, and a break-apart probe for ERG.

Clause 15. The set of probes of clause 14, which further comprises a detectably labeled chromosome enumeration probe for chromosome 8, a detectably labeled chromosome enumeration probe for chromosome 10, a detectably labeled locus-specific probe for AURKA, a detectably labeled locus-specific probe for NKX3.1, a detectably labeled locus-specific probe for P27, and/or a detectably labeled break-apart probe for ETV1.

Clause 16. A set of probes comprising a detectably labeled, locus-specific probe for MYC, a detectably labeled, locus-specific probe for FGFR1, and a detectably labeled, break-apart probe for ERG.

Clause 17. The set of probes of clause 16, which further comprises a detectably labeled, locus-specific probe for PTEN.

Clause 18. The set of probes of clause 16, which further comprises a detectably labeled, locus-specific probe for MYCN.

Clause 19. The set of probes of clause 16, which further comprises a detectably labeled, locus-specific probe for MDM2.

Clause 20. The set of probes of any of clauses 16-19, which further comprises a detectably labeled chromosome enumeration probe for chromosome 8, a detectably labeled chromosome enumeration probe for chromosome 10, a detectably labeled locus-specific probe for AURKA, a detectably labeled locus-specific probe for NKX3.1, a detectably labeled locus-specific probe for P27, and/or a detectably labeled break-apart probe for ETV1.

Clause 21. A kit comprising a set of probes and instructions for carrying out the method of any of clauses 1-5.

Clause 22. A kit comprising a set of probes and instructions for carrying out the method of any of clauses 6-8.

Clause 23. The kit of clause 22, which comprises:

(a) a set of probes that enables identification of a patient with aggressive, prostatic adenocarcinoma, wherein the set of probes comprises a detectably labeled, locus-specific probe for MYC, a detectably labeled, locus-specific probe for FGFR1, and a detectably labeled, break-apart probe for ERG, and (b) instructions for identifying a patient with a high risk of developing aggressive, prostatic adenocarcinoma, wherein the instructions comprise determining in a sample obtained from the patient the presence of chromosomal abnormalities, wherein one or more of a MYC % gain (% gain is % of cells with MYC copy numbers >2) of greater than 14, an FGFR1% loss (% loss is % of cells with FGFR1 copy numbers <2) of greater than 26, and a ERG % 2+Edel of greater than 10 indicates that the patient has a high risk of developing aggressive, prostatic adenocarcinoma.

Clause 24. A kit comprising a set of probes and instructions for carrying out the method of any of clauses 10-12.

Clause 25. The kit of clause 24, which comprises:

(a) a set of probes that enables identification of a patient with indolent, prostatic adenocarcinoma, wherein the set of probes comprises a detectably labeled, locus-specific probe for MYC, a detectably labeled, locus-specific probe for FGFR1, a detectably labeled, break-apart probe for ERG, and a detectably labeled, locus-specific probe for PTEN, and (b) instructions for identifying a patient with indolent, prostatic adenocarcinoma, wherein the instructions comprise determining in a sample obtained from the patient the presence of chromosomal abnormalities, wherein one or more of a MYC % gain (% gain is % of cells with MYC copy numbers >2) of greater than two, an FGFR1% loss (% loss is % of cells with FGFR1 copy numbers <2) of greater than 10, a PTEN % homozygous loss of greater than 20, and a ERG % 2+Edel of greater than 10 indicates that the patient has a high risk of developing aggressive, prostatic adenocarcinoma and none of the foregoing indicates that the patient has indolent, prostatic adenocarcinoma.

What is claimed is:

1. A method comprising determining the copy number of the CMYC, ERG, and FGFR1 genes in a prostate adenocarcinoma sample by contacting the sample with a set of detectably labeled probes consisting of a locus-specific probe for CMYC, an ERG centromeric probe (ERG Cen), an ERG telomeric probe (ERG Tel), and a locus-specific probe for FGFR1 and performing fluorescence in situ hybridization.

2. The method of claim 1, further comprising determining one or more of the Gleason score, tumor stage, and/or prostate-specific antigen (PSA) level of the prostate adenocarcinoma.

3. A method of treating a prostate adenocarcinoma in a human, which method comprises:

(a) contacting a prostate adenocarcinoma sample with a set of detectably labeled probes consisting of a locus-specific probe for CMYC, an ERG centromeric probe (ERG Cen), an ERG telomeric probe (ERG Tel), and a locus-specific probe for FGFR1 and performing fluorescence in situ hybridization;

(b) detecting one or more of (i) a copy number of the CMYC gene that is greater than 2, (ii) duplication of an ERG gene fusion and an interstitial deletion of sequences 5' to the ERG gene (ERG 2+Edel), and/or (iii) a copy number of the FGFR1 gene that is less than 1; and (c) administering to the human one or more of surgery, hormone therapy, radiation, and/or androgen deprivation, whereupon the prostatic adenocarcinoma is treated.

4. The method of claim 3, which comprises detecting two or more of (i) a copy number of the CMYC gene that is greater than 2, (ii) duplication of an ERG gene fusion and an interstitial deletion of sequences 5' to the ERG gene (ERG 2+Edel), and/or (iii) a copy number of the FGFR1 gene that is less than 1.

5. The method of claim 4, which comprises detecting (i) a copy number of the CMYC gene that is greater than 2, (ii) duplication of an ERG gene fusion and an interstitial deletion of sequences 5' to the ERG gene (ERG 2+Edel), and (iii) a copy number of the FGFR1 gene that is less than 1.

6. The method of claim 3, further comprising determining one or more of the Gleason score, tumor stage, prostate-specific antigen (PSA) level, and/or age of the human.

* * * * *